US009387192B2

(12) United States Patent
Li-Weber et al.

(10) Patent No.: US 9,387,192 B2
(45) Date of Patent: Jul. 12, 2016

(54) COMBINATION OF ROCAGLAMIDE AND APOPTOSIS INDUCING SUBSTANCES FOR THE TREATMENT OF CANCER

(75) Inventors: Min Li-Weber, Bad Dürkheim (DE); Peter H. Krammer, Heidelberg (DE)

(73) Assignee: DKFZ DEUTCHERS KREBSFORSCHUNGSZENTRUM, Heidelberg (DE)

( * ) Notice: Subject to any disclaimer, the term of this patent is extended or adjusted under 35 U.S.C. 154(b) by 71 days.

(21) Appl. No.: 13/130,019

(22) PCT Filed: Nov. 20, 2009

(86) PCT No.: PCT/EP2009/065560
§ 371 (c)(1),
(2), (4) Date: Jun. 22, 2011

(87) PCT Pub. No.: WO2010/057981
PCT Pub. Date: May 27, 2010

(65) Prior Publication Data
US 2011/0250166 A1 Oct. 13, 2011

(30) Foreign Application Priority Data

Nov. 20, 2008 (EP) ..................................... 08169536

(51) Int. Cl.
*A61K 31/343* (2006.01)
*A61K 39/395* (2006.01)
*A61K 45/06* (2006.01)

(52) U.S. Cl.
CPC ............. *A61K 31/343* (2013.01); *A61K 39/395* (2013.01); *A61K 45/06* (2013.01)

(58) Field of Classification Search
CPC ............ A61K 2300/00; A61K 31/343; A61K 39/395; A61K 45/06
See application file for complete search history.

(56) References Cited

U.S. PATENT DOCUMENTS

| 3,590,028 | A | 6/1971 | Arcamone et al. | |
|---|---|---|---|---|
| 4,539,414 | A | 9/1985 | King et al. | |
| 2005/0203288 | A1* | 9/2005 | Butz et al. | 536/23.2 |
| 2009/0299081 | A1* | 12/2009 | Porco et al. | 549/354 |

FOREIGN PATENT DOCUMENTS

| WO | WO 95/10273 A1 | 4/1995 |
|---|---|---|
| WO | WO 97/08161 A1 | 3/1997 |
| WO | WO 02/02566 A1 | 1/2001 |
| WO | WO 2005/092876 A1 | 10/2005 |

OTHER PUBLICATIONS

Zhu Jy et al, "The traditional Chinese herbal compound rocaglamide preferentially induces apoptosis in leukemia cells by modulation of mitogen-activated protein kinase activities," Int J Cancer. Oct. 15, 2007;121(8):1839-46.*

Ronald J. Tallarida, "Drug Synergism: Its Detection and Applications," The Journal of Pharmacology and Expeimental Therapeutics (2001) vol. 298:865-872.*
Ashkenazi et al., "Safety and antitumor activity of recombinant soluble Apo2 ligand," J. Clin. Invest., Jul. 1999, pp. 155-162, vol. 104, No. 2.
Baumann et al., "Rocaglamide Derivatives Are Potent Inhibitors of NF-κB Activation in T-cells," J. Biol. Chem., Nov. 2002, pp. 44791-44800, vol. 277, No. 47.
Bohnenstengel et al., "1H-Cyclopenta[b]benzofuran Lignans from *Aglaia* Species Inhibit Cell Proliferation and Alter Cell Cycle Distribution in Human Monocytic Leukemia Cell Lines," 1999, Z. Naturforsch [C], pp. 1075-1083, vol. 54.
Bohnenstengel et al., "Structure Activity Relationships of Antiproliferative Rocaglamide Derivatives from *Aglaia* Species (*Meliaceae*)," 1999, Z. Naturforsch [C], pp. 55-60, vol. 54.
Buchsbaum et al., "TRAIL receptor-targeted therapy," Future Oncol., 2006, pp. 493-508, vol. 2, No. 4.
Buchsbaum et al., "TRAIL-receptor antibodies as a potential cancer treatment," 2007, Future Oncol, pp. 405-409, vol. 3, No. 4.
Carlo-Stella et al., "Targeting TRAIL Agonistic Receptors for Cancer Therapy," Apr. 2007, Clin. Cancer Res., pp. 2313-2317, vol. 13, No. 8.
Chcialowski et al., "Local Administration of Tumor Necrosis Factor alpha in a case of lung tumor," Jun. 1997, pp. 382-384, vol. 2, No. 12. [Eng. Abstract included].
Cosimi et al., "Treatment of Acute Renal Allograft Rejection with OKT3 Monoclonal Antibody," Transplantation, 1981, pp. 535-539, vol. 32, No. 6.
Dhar et al., "Screening of Indian Plants for Biological Activity: Part IV," Indian J. Exp. Biol., Jan. 1973, pp. 43-54, vol. 11.
Glazier et al., "Intravesical Recombinant Tumor Necrosis Factor in the Treatment of Superficial Bladder Cancer: an Eastern Cooperative Oncology Group Study," Jul. 1995, J. Urology, pp. 66-68, vol. 154, No. 1.
Hansen R.M., "5-Fluorouracil by Protracted Venous Infusion: A Review of Recent Clinical Studies," Cancer Invest., 1991, pp. 637-642, vol. 9, No. 6.
Hasegawa et al., "Sensitivity of adult T-cell leukaemia lymphoma cells to tumour necrosis factor-related apoptosis-inducing ligand," British J. Haematology, 2004, pp. 253-265, vol. 128.
Herold et al., "Activation of human T cells by FcR nonbinding anti-CD3 mAb, hOKT3γ1(Ala-Ala)," J. Clin. Invest., Feb. 2003, pp. 409-418, vol. 111, No. 3.
Hwang et al., "Silvestrol and Episilvestrol, Potential Anticancer Rocaglate Derivatives from *Aglaia silvestris*," J. Org. Chem., 2004, pp. 3350-3358, vol. 69, No. 10.
Kim et al., "Potential of Cyclopenta[*b*]benzofurans from *Aglaia* Species in Cancer Chemotherapy," 2006, Anti-Cancer Agents in Med. Chem., pp. 319-345, vol. 6, No. 4.
King et al., "X-Ray Crystal Structure of Rocaglamide, a Novel Antileukemic 1H-Cyclopenta[*b*]benzofuran from *Aglaia elliptifolia*," J. Chem. Soc., Chem. Commun., 1982, pp. 1150-1151, vol. 20.
Krueger et al., "HTLV-1 Tax protects against CD95-mediated apoptosis by induction of the cellular Flice-inhibitory protein (c-FLIP)," Blood, May 2006, pp. 3933-3939, vol. 107, No. 10.

(Continued)

*Primary Examiner* — Thomas S Heard
(74) *Attorney, Agent, or Firm* — Foley & Lardner LLP

(57) ABSTRACT

The present invention relates to a combined preparation comprising at least one rocaglamide derivative and at least one apoptosis inducing agent, preferably from the group of substances comprising agents inducing the extrinsic apoptotic pathway, antiproliferative agents and agents which induce apoptosis in T-cells by activation induced cell death (AICD) for the treatment of cancer.

12 Claims, 15 Drawing Sheets

(56) References Cited

OTHER PUBLICATIONS

Figure 1:
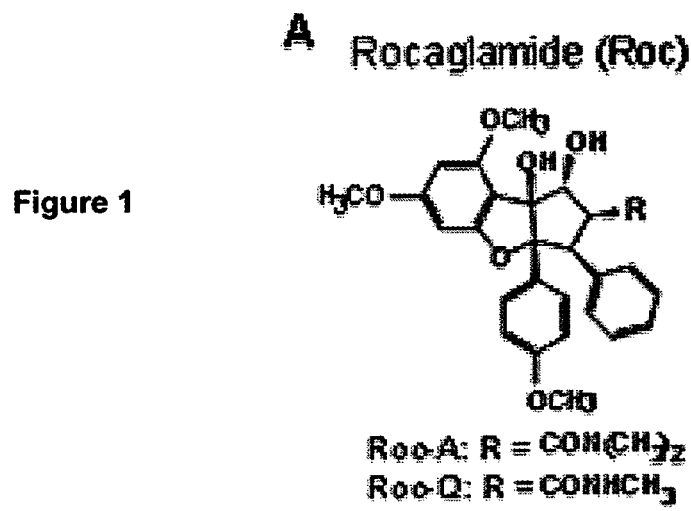
Figure 1:
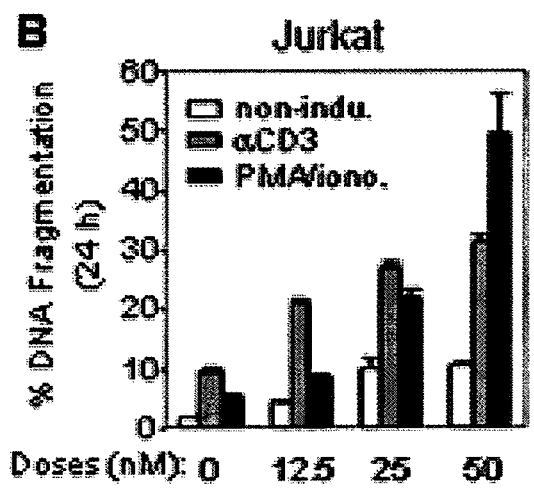
Figure 1:
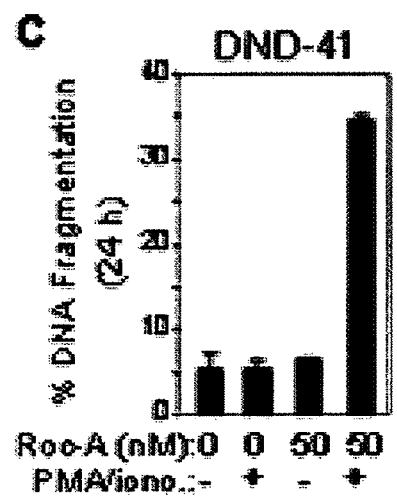
Figure 1:
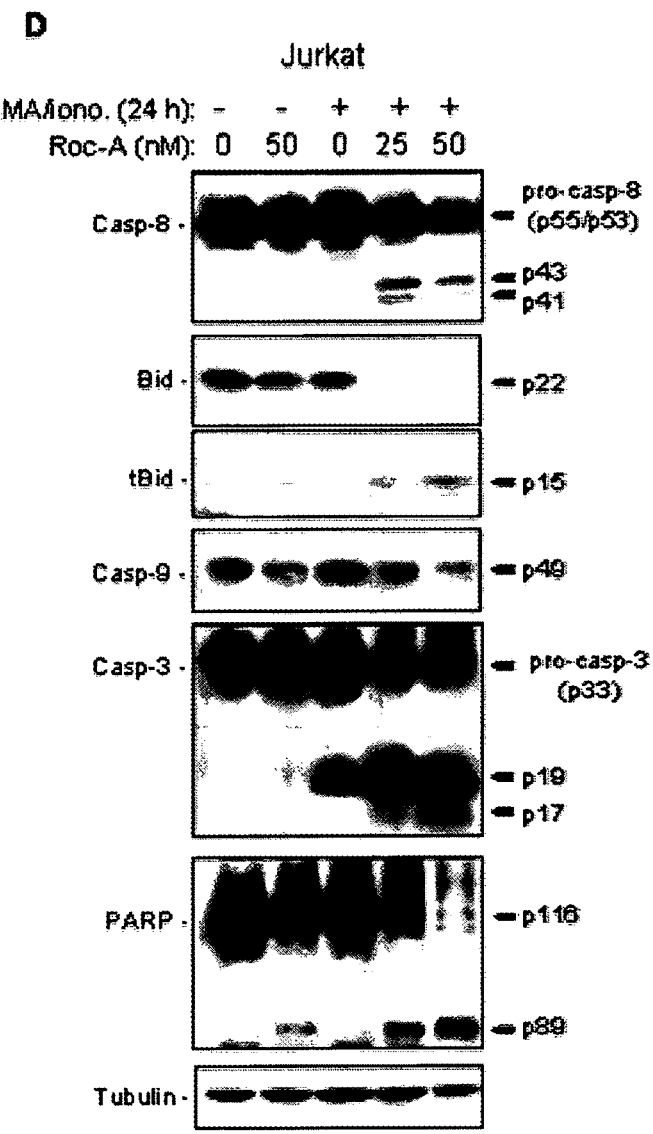
Figure 1:
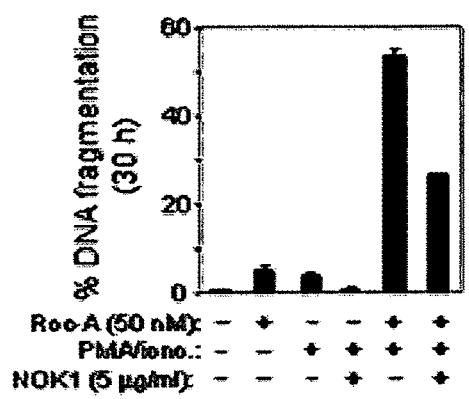
Figure 1:
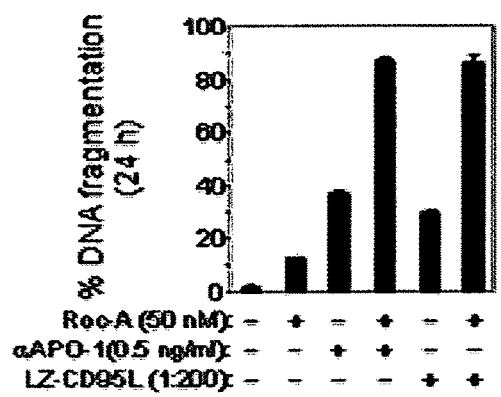

Lee et al., "Cytostatic mechanism and antitumor potential of novel 1*H*-cyclopenta[*b*]benzofuran lignans isolated from *Aglaia elliptica*," Chem. Biol. Interact., 1998, pp. 215-228, vol. 115.

Lund et al., "Clinical and preclinical activity of 2',2'-difluorodeoxycytidine (gemcitabine)," Cancer Treatment Reviews, 1993, pp. 45-55, vol. 19, No. 1.

Matsuda et al., "Resistance to Apo2 Ligand (Apo2L)/Tumor necrosis Factor-Related Apoptosis-Inducing Ligand (TRAIL)-Mediated Apoptosis and Constitutive Expression of Apo2L/TRAIL in Human T-Cell Leukemia Virus Type 1-Infected T-Cell Lines," J. Virology, Feb. 2005, pp. 1367-1378, vol. 79, No. 3 (Retracted).

Matsuoka et al., "Human T-cell leukaemia virus type 1 (HTLV-1) infectivity and cellular transformation," Nature, Reviews, Apr. 2007, pp. 270-280, vol. 7.

Goldstein et al., Ortho Multicenter Transplant Study Group, "A Randomized Clinical Trial of OKT3 Monoclonal Antibody for Acute Rejection of Cadaveric Renal Transplants," NEJM, Aug. 1985, pp. 337-342, vol. 313, No. 6.

Popma et al., "Anti-CD3 antibodies OKT3 and hOKT3γ1(Ala-Ala) induce proliferation of T cells but impair expansion of alloreactive T cells; a specific T cell proliferation induced by Anti-CD3 antibodies correlates with impaired expansion of alloreactive T cells," 2005, Int. Immunopharmcol., pp. 155-162, vol. 5.

Pui et al., Treatment of Acute Lymphoblastic Leukemia, NEJM, Jan. 2006, pp. 166-178, 354:2.

Shoham et al., "Differential Toxicity on Normal and Transformed Cells in vitro and Inhibition of Tumour Development in vivo by Concanavalin A," Sep. 1970, Nature, pp. 1244-1246, vol. 227, No. 5264.

Woodle et al., "Phase I Trial of a Humanized, Fc Receptor Nonbinding OKT3 Antibody, huOKT3[gamma]$_1$ (Ala-Ala) in the Treatment of Acute Renal Allograft Rejection," 1999, Transplantation, pp. 608-616, vol. 68, No. 5.

International Search Report, PCT/EP2009/065560, completed Feb. 9, 2010, 7 pages.

International Preliminary Report on Patentability and Written Opinion cited in related International Patent Application No. PCT/EP09/065560, Jun. 3, 2011.

European Communication issued in related European Patent Application No. 09752868 dated Jul. 14, 2015.

* cited by examiner

E

F

SEQUENCE LISTING

```
<160> NUMBER OF SEQ ID NOS: 1

<210> SEQ ID NO 1
<211> LENGTH: 17
<212> TYPE: DNA
<213> ORGANISM: artificial
<220> FEATURE:
<223> OTHER INFORMATION: AP-1 binding site from the SV40 enhancer

<400> SEQUENCE: 1
cggttgctga ctaattg                                                    17
```

COMBINATION OF ROCAGLAMIDE AND APOPTOSIS INDUCING SUBSTANCES FOR THE TREATMENT OF CANCER

The present invention relates to a combined preparation comprising at least one rocaglamide derivative and at least one apoptosis inducing agent, preferably from the group of substances comprising agents inducing the extrinsic apoptotic pathway, antiproliferative agents and agents which induce apoptosis in T-cells by activation induced cell death (AICD) for the treatment of cancer.

Cancer constitutes the fourth leading cause of death in Western countries. As the average age in the Western population steadily rises, so do cancer-related deaths indicating that cancer will be one of the most common causes of death in the 21$^{st}$ century. The aggressive cancer cell phenotype is the result of a variety of genetic and epigenetic alterations leading to deregulation of intracellular signaling pathways. Cancer cells commonly fail to undergo so-called "programmed cell death" or "apoptosis", a signaling process that plays a key role in preventing cell tissues from abnormal growth.

Hematological malignancies are cancers that primarily affect cells in blood, bone marrow, spleen and lymph nodes. They are caused by abnormal proliferation of cells of the immune system or their precursor cells. There are two subtypes of haematological malignancies, leukemia and lymphoma.

Leukemia is characterized by an overproduction of blood cells, usually leukocytes. Lymphoblastic leukemia is caused by the abnormal proliferation of lymphocytes. The major types of lymphocytes are the T-lymphocytes, B-lymphocytes and natural killer cells. Myeloid leukemia is caused by abnormal proliferation of bone marrow derived myeloid cells. Both types of leukemia can be separated into chronic and acute diseases. Acute forms of leukemia are characterized by the rapid build up of relatively immature cell types. They usually progress rapidly and kill the patient within a few weeks or months after diagnosis if left untreated. Acute lymphoblastic leukemia (ALL) is the most common type of childhood cancer. Chronic forms of leukemia are caused by relatively well differentiated cells. They often progress only slowly over years. In many cases it is sufficient to monitor the progress of the disease and to initiate treatment only when the symptoms start to impair the patient's quality of life.

A special type of leukaemia is human T-cell leukemia virus type I (HTLV-1)-associated adult T-cell leukemia/lymphoma (ATL). This is a malignancy of the clonal proliferation of infected mature CD4$^+$ T-cells. Primary HTLV-1-ATL samples and ATL cell lines derived from HTLV-1-infected patients are more resistant to TRAIL- and CD95L-mediated apoptosis as compared to non-HTLV-infected leukemic cells (Hasegawa H et al., 2005, British Journal of Haematology, 128: 253-265; Krueger et al., 2006, Blood 107: 3933-3939; Matsuda et al., 2005, Journal of Virology 79: 1367-1378). Worldwide HTLV-1 has infected 15-20 million people. Patients have a poor prognosis after disease development with a survival range of less than one year (Matsuoka and Jeang, 2007, Nature Reviews Cancer 7: 270-280).

Three modes of cancer therapy are available. Curative surgery attempts to remove the tumor completely. This is only possible as long as there are no metastases. Sometimes surgery may be an option for the treatment of metastases if there are only few and they are easily accessible. Radiotherapy uses ionizing radiation, typically γ-radiation, to destroy the tumor. Radiation therapy is based on the principle that tumor cells with their high metabolic rates are especially susceptible to radiation induced cell damage. The anti-tumor effect of radiation therapy has to be weighted against the damage to the surrounding healthy tissue. Thus, possible tissue damage can rule out this option in some cases due to the damage to healthy tissues to be feared. Furthermore, radiation therapy is limited to cases where the primary tumor has not yet spread or where only few metastases are present. Radiation therapy is used for the treatment of some lymphomas. In Patients with ALL it is often used to prevent the spread of cancer cells into the central nervous system.

The most commonly used—and in many instances the only available—systemic treatment for cancer is chemotherapy. For patients suffering from leukaemia or metastases of solid tumors chemotherapy, thus, is the only treatment option. Chemotherapeutic agents are cytotoxic for all rapidly dividing cells. As cancer cells usually divide more rapidly than other cells in the body, they are preferably killed by these agents. Common groups of chemotherapeutic agents are substances that inhibit cell division by interfering with the formation of the mitotic spindle or agents which damage the DNA, e.g. by alkylating the bases. Because all rapidly dividing cells are targeted by chemotherapeutic agents, their side effects are usually severe. Depending on the substance used they include organ toxicity (e.g. heart or kidney), immunosuppression, neurotoxicity and anaemia. Some groups of chemotherapeutic agents, e.g. alkylating agents, even have the potential to cause cancer. Due to these side effects dosages have sometimes to be reduced or chemotherapy has to be discontinued completely. Furthermore, the side effects chemotherapy often prohibit the treatment of patients in bad general condition. Adding to all these problems is the often limited efficacy of chemotherapy. In some cases chemotherapy fails from the very beginning. In other cases tumor cells become resistant during the course of treatment. To combat the emergence of resistant tumor cells and to limit the side effects of chemotherapy combinations of different compounds with different modes of action are used. Nevertheless, the success of chemotherapy has been limited, especially in the treatment of solid tumors. However, in a few types of cancer, e.g. childhood ALL, the cure rates are relatively high (approximately 80%) (Pui and Evens, 2006, N. Engl. J. Med. 354: 166-178). For these cancers research focuses on means to reduce the undesired side effects without compromising the efficacy of the treatment.

Haematological cancers may sometimes be treated successfully by allogenic bone marrow transplantation. The leukemic cells and the hematopoetic stem cells of the patient are completely eradicated by a combination of whole body irradiation and high dosages of chemotherapeutic agents. The patient then receives hematopoetic stem cells from a suitable donor to rebuild the patient's hematopoetic system. Nevertheless, despite careful genetic selection of the donor the transplanted leukocytes may attack cells of the host leading to graft-versus-host disease. This is a major risk associated with allogenic bone marrow transplantation. Infection is another major risk and a significant cause of mortality after bone marrow transplantation, because the patient almost completely lacks white blood cells for several weeks after the transplantation and thus has no defense against pathogens.

Recently, drugs have become available whose mode of action is not based on toxicity against rapidly dividing cells. These compounds show a higher specificity for cancer cells and thus less side effects than conventional chemotherapeutic agents. Imatinib is used for the specific treatment of chronic myelogenous leukemia. This compound specifically inhibits an abnormal tyrosin kinase which is the product of a fusion gene of bcr and abl. Because this kinase does not occur in non-malignant cells, treatment with Imatinib has only mild side effects. However, Imatinib is not used for the treatment of haematological cancers other than myelogenous leukemia. Rituximab is a monoclonal antibody directed against the cluster of differentiation 20 (CD20), which is widely expressed on B-cells. It is used for the treatment of B cell lymphomas in combination with conventional chemotherapy.

One import mode of action of chemotherapeutic agents is the induction of apoptosis. Many chemotherapeutic agents, e.g. alkylating agents, crosslinking agents or antimetabolites induce DNA damage which finally leads to apoptosis of the affected cells. The often poor efficacy of chemotherapeutic agents in tumor cells can be explained by the disruption of normal apoptotic pathways. Cells in many tumors, for instance, lack a functional copy of p53. The product of this gene is responsible for controlling the cell cycle and initiating DNA-repair in the case of DNA damage. In cells with large scale DNA damage p53 induces apoptosis. Without a functional p53 gene cells progress through the cell cycle and proliferate despite DNA-damage.

Apoptosis pathways involve diverse groups of molecules. One set of mediators implicated in apoptosis are so-called caspases, cysteine proteases that cleave their substrates specifically at aspartate residues. Caspases convey the apoptotic signal in a proteolytic cascade, with caspases cleaving and activating other caspases which subsequently degrade a number of target death proteins, such as poly(ADP-ribose) polymerase, eventually resulting in cell death. If one or more steps in this cascade are inhibited in tumor cells, these cells fail to undergo apoptosis and, thus, continue to grow. Caspase activation itself can be triggered by external stimuli affecting certain cell surface receptors, known to the person skilled in the art as so-called death receptors, or by intracellular stress response via the mitochondria leading to the release of mitochondrial proteins. Extensive DNA damage is one of the factors that activate the intrinsic apoptotic pathway. Known death receptors mediating apoptosis include members of the tumor necrosis factor (TNF) receptor superfamily such as CD95 (APO-1/Fas) or TRAIL (TNF-related apoptosis inducing ligand) receptors 1 and 2. Stimulation of the death receptor CD95 leads to the formation of a cell membrane death inducing signaling complex (DISC, comprising CD95, FADD, pro-caspase 8 and c-FLIP) and among others, to the activation of caspase-8, which in turn activates other caspases and members of another group of apoptosis mediators. In addition, Bcl-2 family members are thought to regulate the release of the mitochondrial proteins and, thus, link the extrinsic death receptor and the mitochondrial pathways together.

Rocaglamide belongs to the group of 1H-cyclopenta[b]benzofurans. Rocaglamide and rocaglamide derivatives can be isolated from *Aglaia* Species. It has been demonstrated that they possess antiproliferative activity (see e.g. U.S. Pat. No. 4,539,414; Dhar et al., 1973 Indian J Exp Vol. 11, pages 43-54; King et al., 1982 J Chem Soc Chem Comm Vol. 20, pages 1150-1151; Lee et al., 1998 Chem Biol Interact Vol. 115, pages 215-228; Bohnenstengel et al., 1999, Z. Naturforsch [C]. Vol. 54, pages 55-60; Bohnenstaengel et al., 1999 Z Naturforsch [C] Vol 54, pages 1075-1083; Kim et al., 2006 Anticancer Agents Med Chem. Vol. 6; pages 319-345).

Rocaglamide derivatives have been shown to have an inhibitory effect on growth of a murine leukaemia cell line (P-388) and a human breast cancer cell line (BC1) in vitro and also in vivo (Hwang et al., 204, J. Org. Chem. 69:3350-3358; Lee et al., 1998, Chem. Biol. Interact 115: 215-228)

Obviously, there is great need for generally applicable systemic cancer treatments with increased efficacy and reduced side effects as compared to traditional chemotherapy.

The present invention provides means to increase the efficacy of conventional chemotherapy as well as of other systemic cancer treatments.

The problem of the present invention is therefore solved by a combined preparation for simultaneous, separate or sequential use comprising a) at least one rocaglamide derivative of the formula (I) and/or a pharmaceutically acceptable salt thereof and b) one apoptosis inducing agent, preferably from the group of substances comprising agents inducing the extrinsic apoptotic pathway, antiproliferative agents and agents which induce apoptosis in T-cells by activation induced cell death (AICD) or a pharmaceutically acceptable salt thereof,

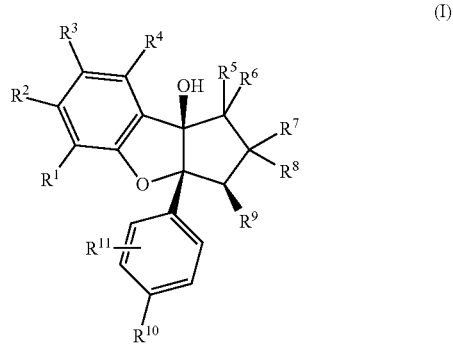

(I)

wherein
$R^1$ is selected from hydrogen, halogen and alkyl;
$R^2$ is selected from halogen, alkyl and alkoxy;
$R^3$ is selected from hydrogen, halogen and alkyl;
$R^4$ is selected from halogen, alkyl and alkoxy;
or $R^2$ and $R^3$ together form a —OCH$_2$CH$_2$O— unit;
$R^5$ is selected from hydroxy, acyloxy, amino, monoalkylamino, dialkylamino and —NR$^{12}$—CHR$^{13}$—COOR$^{14}$, with $R^{12}$ being selected from hydrogen and alkyl,
$R^{13}$ being selected from phenyl and benzyl, which both may carry a substituent from the group hydroxy, indolyl and imidazolylmethyl, and alkyl which may be substituted by a group selected from OH, SH, alkoxy, thioalkoxy, amino, monoalkylamino, dialkylamino, carboxy, carboxyalkyl, carboxamide and guanidino groups;
or $R^{12}$ and $R^{13}$ together form a —(CH$_2$)$_3$— or —(CH$_2$)$_4$— group;
$R^{14}$ being selected from alkyl and benzyl;
in which case $R^6$ is hydrogen; or
$R^5$ and $R^6$ together form an oxo or hydroxyimino group;
$R^7$ is hydrogen;
$R^8$ is selected from hydrogen, —COOR$^{15}$ and CONR$^{16}$R$^{17}$, wherein
$R^{15}$ and $R^{16}$ are independently selected from hydrogen and methyl, and
$R^{17}$ is selected from hydrogen, methyl, 4-hydroxybutyl and 2-tetrahydrofuryl;
$R^9$ is selected from phenyl which is optionally substituted, and hetaryl which is optionally substituted;
$R^{10}$ is selected from hydrogen, halogen, alkyl and alkoxy, and
$R^{11}$ is selected from hydrogen, hydroxy, halogen, alkoxy and alkyl; or
$R^{10}$ and $R^{11}$ are in ortho-position to each other and together form a —OCH$_2$O— unit.

The term "alkyl", as mentioned in the above definitions of the substituents $R^1$ to $R^{17}$, in each case refers to a substituted or an unsubstituted, linear or branched, acyclic or cyclic alkyl group, preferably an unsubstituted linear or branched acyclic alkyl group. Furthermore, the term "alkyl", as mentioned in the above definitions of the substituents $R^1$ to $R^{17}$, in each case preferably refers to a $C_1$- to $C_4$-alkyl group, namely methyl, ethyl, i-propyl, n-propyl, n-butyl, i-butyl, sec-butyl or tert-butyl. The above also applies when "alkyl" is used in "alkylamino" and "dialkylamino" and other terms containing the term "alkyl".

The term "alkoxy", as mentioned in the above definitions of the substituents $R^1$ to $R^{17}$, in each case refers to a substituted or an unsubstituted linear or branched, acyclic or cyclic alkoxy group, preferably an unsubstituted linear or branched acyclic alkoxy group. Furthermore, the term "alkoxy", as mentioned in the above definitions of the substituents $R^1$ to $R^{17}$, in each case preferably refers to a $C_1$- to $C_4$-alkoxy group, namely methoxy, ethoxy, i-propyloxy, n-propyloxy, n-butyloxy, i-butyloxy, sec-butyloxy or tert-butyloxy.

The above also applies when "alkoxy" is used in "thioalkoxy" and other terms containing the term "alkoxy".

The term "acyloxy", as mentioned in the above definitions of the substituents $R^1$ to $R^{17}$, in each case refers to a substituted or an unsubstituted linear or branched, acyclic or cyclic acyloxy group, preferably an unsubstituted linear or branched acyclic acyloxy group. Furthermore, the term "acyloxy", as mentioned in the above definitions of the substituents $R^1$ to $R^{17}$, in each case preferably refers to a $C_1$- to $C_4$-acyloxy group, namely formyloxy, acetoxy, i-propyloxy, n-propyloxy, n-butyloxy, i-butyloxy, sec-butyloxy or tert-butyloxy.

The term "hetaryl" as used in the above definition refers to a 5-, 6- or 7-membered carbocyclic saturated or non-saturated, aromatic or non-aromatic ring which may carry in the ring one or more heteroatoms from the group O, S, P, N.

In a preferred embodiment of the present invention, the substituents $R^1$ to $R^{14}$ have the following meanings.

$R^1$ and $R^3$ each are hydrogen;
$R^2$ and $R^4$ each are independently selected from methoxy which is optionally substituted;
$R^5$ is selected from hydroxy, formyloxy and acetyloxy, alkylamino, $-NR^{12}-CHR^{13}-COOR^{14}$, with
$R^{12}$ being selected from hydrogen and alkyl,
$R^{13}$ being selected from: alkyl which may be substituted by: a group selected from OH, SH, alkoxy; thioalkoxy, amino, monoalkylamino, dialkylamino, carboxy, carboxyalkyl, carboxamide and guanidino groups; and phenyl and benzyl, which both may carry a substituent from the group hydroxy, indolyl and imidazolylmethyl;
$R^{14}$ being selected from alkyl and benzyl;
$R^6$ is hydrogen;
$R^7$ is hydrogen;
$R^8$ is selected from hydrogen, $-COOCH_3$ and $CON(CH_3)_2$;
$R^9$ is phenyl which is optionally substituted;
$R^{10}$ is methoxy;
$R^{11}$ is selected from hydrogen and hydroxy, or
$R^{10}$ and $R^{11}$ are in ortho-position to each other and together form a $-OCH_2O-$ unit.

In a more preferred embodiment of the present invention, the rocaglamide derivatives of the present invention refer to those of formula (I) wherein
$R^1$ and $R^3$ each are hydrogen,
$R^2$ and $R^4$ each are optionally substituted methoxy,
$R^5$ is hydroxy or $-NR^{12}-CHR^{13}-COOR^{14}$, with
$R^{12}$ being selected from hydrogen and alkyl,
$R^{13}$ being selected from: alkyl which may be substituted by: a group selected from OH, SH, alkoxy; thioalkoxy, amino, monoalkylamino, dialkylamino, carboxy, carboxyalkyl, carboxamide and guanidino groups; and phenyl and benzyl, which both may carry a substituent from the group hydroxy, indolyl and imidazolylmethyl;
$R^{14}$ being selected from alkyl and benzyl;
$R^6$ and $R^7$ each are hydrogen,
$R^8$ is $-CON(CH_3)_2$,
$R^9$ is optionally substituted phenyl,
$R^{10}$ is methoxy and
$R^{11}$ is hydrogen; or wherein
$R^1$ and $R^3$ each are hydrogen,
$R^2$ and $R^4$ each optionally substituted methoxy,
$R^5$ is acetoxy or $-NR^{12}-CHR^{13}-COOR^{14}$, with
$R^{12}$ being selected from hydrogen and alkyl,
$R^{13}$ being selected from: alkyl which may be substituted by: a group selected from OH, SH, alkoxy; thioalkoxy, amino, monoalkylamino, dialkylamino, carboxy, carboxyalkyl, carboxamide and guanidino groups; and phenyl and benzyl, which both may carry a substituent from the group hydroxy, indolyl and imidazolylmethyl;
$R^{14}$ being selected from alkyl and benzyl;
$R^6$ and $R^7$ each are hydrogen,
$R^8$ is $-CON(CH_3)_2$,
$R^9$ is optionally substituted phenyl,
$R^{10}$ is methoxy and
$R^{11}$ is hydrogen; or wherein
$R^1$ and $R^3$ each are hydrogen,
$R^2$ and $R^4$ each optionally substituted methoxy,
$R^5$ is formyloxy or $-NR^{12}-CHR^{13}-COOR^{14}$, with
$R^{12}$ being selected from hydrogen and alkyl,
$R^{13}$ being selected from: alkyl which may be substituted by: a group selected from OH, SH, alkoxy; thioalkoxy, amino, monoalkylamino, dialkylamino, carboxy, carboxyalkyl, carboxamide and guanidino groups; and phenyl and benzyl, which both may carry a substituent from the group hydroxy, indolyl and imidazolylmethyl;
$R^{14}$ being selected from alkyl and benzyl;
$R^6$ and $R^7$ each are hydrogen,
$R^8$ is hydrogen or $-COOCH_3$,
$R^9$ is optionally substituted phenyl, and
$R^{10}$ and $R^{11}$ are in ortho-position to each other and together form a $-OCH_2O-$ unit.

In a further embodiment of the present invention, $R^8$ is a group of the formula In still a further embodiment of the present invention, $R^5$ and $R^8$ together form a group of the formulae (a)

or (b)

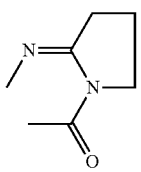

wherein
R⁵ is connected to the nitrogen.

As used herein, the term "rocaglamide derivative(s)" refers to cyclopenta[b]tetrahydrobenzofuran derivatives having the general formula (I). Examples of such compounds include compounds such as rocaglamide, aglaroxin C, cyclorocaglamide, rocaglaol, methylrocaglate (aglafolin), desmethylrocaglamide, pannellin and the recently isolated dioxanyloxy-modified derivatives silvestrol and episilvestrol (Hwang et al., 2004, J. Org. Chem. Vol. 69: pages 3350-3358). Most preferably, the rocaglamide derivatives contemplated for the purposes of the present invention are those of formula (II) (named Roc-A in the example section), formula (III), formula (IV), formula (V) (named Roc-Q in the example section) and formula (VI) (referred to as Roc-AR in the present application).

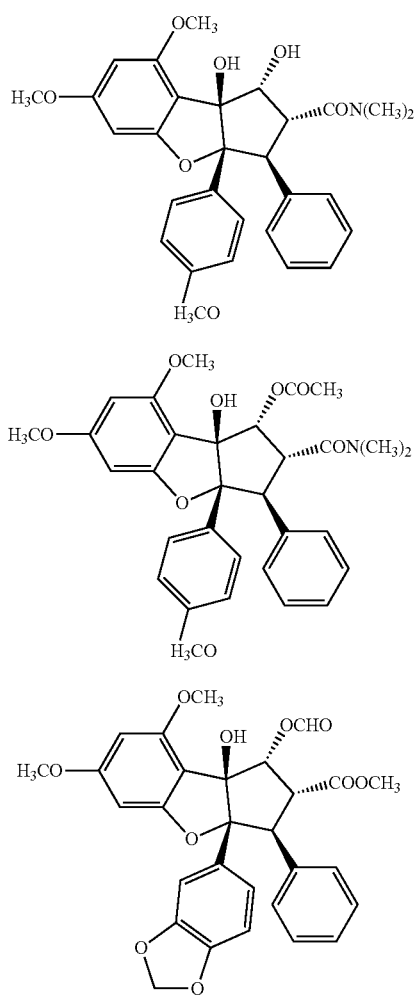

(VI)

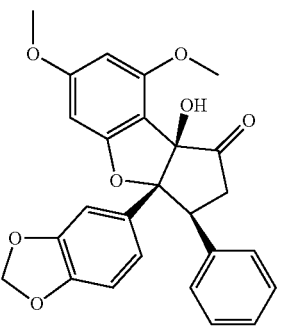

For the preparation of the rocaglamide derivatives according to the present invention, reference is made to WO 00/07579, WO 03/045375 and WO 00/08007.

Some of the compounds of the invention and/or salts or esters thereof will exist in different stereoisomeric forms. All of these forms are included in the present invention.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977), which is incorporated herein by reference. The salts can be prepared in situ during the final isolation and purification of the rocaglamide derivatives, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

A "combined preparation" as referred to in this application preferably comprises all pharmaceutically active compounds in one preparation so that all compounds are administered simultaneously and in the same way.

Also preferably, the combined preparation comprises at least two physically separated preparations for separate administration, wherein each preparation contains at least one pharmaceutically active compound. The latter alternative is preferred in cases where the pharmaceutically active compounds of the combined preparation have to be administered by different routes, e.g. parenterally and orally, due to their chemical or physiological properties.

Preferably, the at least two separated preparations are administered simultaneously. This means that the time frames of the administration of the preparations overlap.

Also preferred is the sequential administration of the at least two preparations, whereas the administration of the single preparations shall occur in time frames which do not overlap so that the at least to pharmaceutically active compounds of the preparations are present in such plasma concentrations which enable the synergistic effect of the present invention. Preferably, the at least two preparations are administered in a time interval of 1 minute, 5 minutes, 15 minutes, 30 minutes, 1 hour, 2 hours, 4 hours, 8 hours, 16 hours, 1 day or 2 days.

The term "treating" refers to ameliorating the diseases or disorders referred to herein or the symptoms accompanied therewith to a significant extent. Said treating as used herein also includes an entire restoration of the health with respect to the diseases or disorders referred to herein. As used herein, the term "treatment" as used in relation to the treatment of cancer is to be understood as embracing both symptomatic and prophylactic modes, that is the immediate treatment, e.g. of acute cancer (symptomatic treatment) as well as advance treatment to prevent, ameliorate or restrict long term symptomatology (prophylactic treatment). The term "treatment" as used in the present specification and claims in relation to such diseases is to be interpreted accordingly as including both symptomatic and prophylactic treatment, e.g., in the case of cancer, symptomatic treatment to reduce the tumor size, preferably to kill all tumor cells, and prophylactic treatment to inhibit the formation of new cancer cells. It is to be understood that treating as used in accordance with the present invention may not be effective in all subjects to be treated. However, the term shall require that a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population.

Preferred antiproliferative agents are chemotherapeutic agents. These substances lead to cell damage, e.g. to the DNA. This damage induces apoptosis of the cell via the intrinsic pathway. They are known to the person skilled in the art.

Preferred chemotherapeutic agents are selected from the group consisting of antimetabolites, Bleomycins, DNA-crosslinking agents, Anthracyclines, topoisomerase poisons, monoclonal antibodies, biological response modifiers, tyrosine kinase inhibitors, aromatase inhibitors, aurora kinase inhibitors, histone deacetylase inhibitors, metalloprotease inhibitors, RAS-MAPK inhibitors, enzymes and spindle poisons. More preferably, the chemotherapeutic agent is selected from the antimetabolites and Anthracylines.

Preferred antimetabolites are methotrexate, 6-mercaptopurine, fludarabine, cladribine, 5-fluorouracil, capecitabine, cytarabine, gemcitabine and hydroxyurea. A preferred bleomycin is bleomycin. Preferred DNA-crosslinking agents are cisplatin, carboplatin and oxaliplatin. Preferred DNA-alkylating agents are mechlorethamine, chlorambucil, cyclophosphamide, melphalan, ifosfamide, procarbazine, dacarbazine, temozolomide, carmustine and lomustine. Preferred anthracyclines are daunorubicin, doxorubicin, epirubicin and idarubicin. Preferred topoisomerase poisons are etoposide, irinotecan, topotecan, teniposide, 9-NC, rubitecan, 9-AC, IDEC-132, exatecan mesylate (DX-8591f), DE-310, lurtotecan GI-147211, gimatecan (ST-1481), PEG-camptothecin, prothecan, karenitecin, BNP-1350, silatecan, DB-67, diflomotecan, BN 80915 and mitoxantrone. Preferred monoclonal antibodies include gemtuzumab, alemtuzumab, ibritumomab tiuxetan, tositumomab, iodine-131 tositumomb, rituximab, trastuzumab, cetuximab, panitumumab, pertuzumab, Cetuximab and bevacizumab. A preferred biological response modifier is interferon-$\alpha$. Preferred aromatase inhibitors are aminoglutethimide, androstenedlone, formestane, exemestane, anastrozole and letrozole. Preferred aurora kinase inhibitors are ZM447439 and VX-680. Preferred histone deacetylase inhibitors are depsipeptide (FK-228), apicidin, trichostatin A (TSA), sodium butyrate, AN-9 (Pivanex), PXD-101, sulfonamide hydroxamic acid, MS-275, and tubacin. Preferred RAS-MAPK inhibitors are R115577 (zarnestra), SCH66336 (sarasar), BAY 43-9006, CL-1040, PD0325901 and ARRY-142886. Preferred tyrosine kinase inhibitors are imatinib, dasatinib, nilotibib, sunitinib, sorafenib, lapatinib, gefitinib, AE788, CI-1033, EXEL 7647/EXEL 0999, ERB-569 and erlotinib. A preferred enzyme is asparaginase. Preferred hormones are tamoxifen, leuprolide acetate, megestrol acetate, flutamide and bicalutamide, anastrozole, exemestane and letrozole. Preferred spindle poisons are vinblastine, vincristine, vinorelbine, paclitaxel and docetaxel.

Especially preferred chemotherapeutic agents are gemcitabine, doxorubicin and 5-fluorouracil.

The term "agents inducing the extrinsic apoptotic pathway" refers to substances that induce apoptosis by binding to death receptors. Preferred ligands of death receptors are tumor necrosis factor $\alpha$ (TNF-$\alpha$), tumor necrosis factor (TNF-$\beta$, lymphotoxin $\alpha$), lymphotoxin $\beta$ (LT-$\beta$), TRAIL (Apo2L), CD95 (Fas, APO-1) ligand, TRAMP (DR3, Apo-3) ligand, DR4 ligand, DR6 ligand as well as fragments and derivatives of said ligands. An especially preferred agent inducing the extrinsic apoptotic pathway is TRAIL (Apo2L). Even more preferred is Superkiller-TRAIL as described by Wang A et al., 2004 (Cancer Cell 5: 501). The person skilled in the art knows that the aforementioned proteins may be produced using standard techniques for the production of recombinant proteins.

Also preferred ligands of death receptors are antibodies directed against death receptors, preferably anti-CD95 antibody, anti-TRAIL-R1 (DR4) antibody, anti-TRAIL-R2 (DR5) antibody, anti-DR6 antibody, anti TNF-R1/2 antibody and anti-TRAMP (DR3) antibody as well as fragments or derivatives thereof.

A "therapeutically effective amount" of a rocaglamide derivative is the amount of a rocaglamide derivative that is required to treat cancer in combination with at least one apoptosis inducing or antiproliferative agent. It is known to the person skilled in the art that the therapeutically effective amount of a drug depends on the route of administration. If the rocaglamide derivative is injected, the therapeutically effective amount ranges, preferably, from 0.1 mg/kg to 300 mg/kg, more preferably from 0.1 mg/kg to 50 mg/kg body weight, most preferably from 0.1 mg/kg to 10 mg/kg.

Preferably, a therapeutically effective amount of an apoptosis inducing or antiproliferative agent is an amount that is sufficient to kill cancer cells. The exact dosage depends on the type of cancer to be treated, the medicaments to be used and the route of administration. The person skilled in the art knows how to decide which amounts are to be used. This option is preferred, if it is intended to increase the therapeutical effect of the antiproliferative or apoptosis inducing agents.

The therapeutically effective amount for gemcitabine ranges, preferably, from 1000 to 1500 mg/m$^2$, more preferably from 500 to 2000 mg/m$^2$.

Also preferably, the amounts of antiproliferative or apoptosis inducing agents used in combination with at least one rocaglamide derivative according to the present invention can be decreased as compared to the amounts administered without a rocaglamide derivative. This option is preferred, if it is intended to reduce the side effects of the antiproliferative or apoptosis inducing agents.

According to the present invention the subject to be treated shall suffer from cancer. Preferably, the subject to be treated is a mammal, more preferably it is a rodent or a primate, most preferably it is a human.

The term "cancer" refers to solid tumors as well as cancers of the blood. Preferred cancer types to be treated with the combination of at least one rocaglamide derivative and at least one chemotherapeutic agent are neuroblastoma, intestine carcinoma such as rectum carcinoma, colon carcinoma, familiarly adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeolid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, plasmocytoma and human T-cell leukemia virus type 1 (HTLV-1)-associated adult T-cell leukemia/lymphoma (ATL).

Especially preferred are hematological cancers, i.e. leukemia, hodgkin lymphoma (also known as hodgkin disease), colon carcinoma, hepatic carcinoma and pancreatic carcinoma. Most preferred is human T-cell leukemia virus type 1 (HTLV-1)-associated adult T-cell leukemia/lymphoma (ATL).

The combined use of at least one rocaglamide derivative and at least one chemotherapeutic agent is especially preferred in cancers that respond poorly to conventional chemotherapy alone. Preferably, cells of such cancers display resistance against one or more of the chemotherapeutic agents used. Resistance means that the cells can survive or even proliferate further in a subject even though the subject is treated with the usual amounts of the chemotherapeutic agent or agents in question.

Also preferably, the combination of at least one rocaglamide derivative and at least one chemotherapeutic agent is used against cancers whose poor response to apoptosis inducing or antiproliferative agents is caused by the impairment of intracellular signalling pathways that induce apoptosis, preferably by a mutation of p53.

Advantageously, the combination of at least one rocaglamide derivative and at least one chemotherapeutic agent can be used to increase the efficacy of the currently used chemotherapeutic agents. It has been found that the combination of a rocaglamide derivative with a chemotherapeutical agent synergistically enhances the effects of the chemotherapeutic agent. Two applications of this mechanism are possible.

The chemotherapeutic agents can be applied in dosages that are currently used in conventional treatment protocols. This approach promises to increase the effect of conventional treatment protocols for chemotherapy, i.e. the rate of successfully treated patients can be expected to rise. Furthermore, patients with tumors that are resistant to the currently used dosages of chemotherapeutic agents may profit from the combination therapy because rocaglamide derivatives increase the effect of the currently used chemotherapeutic agents.

Also possible is a second approach, wherein the chemotherapeutic agents are used in decreased dosages and still retain their efficacy due to the combination with at least one rocaglamide derivative. Treatment protocols that require reduced dosages of chemotherapeutic agents have the potential to reduce the undesired and often severe side effects of chemotherapy. Thus, a combination therapy with a rocaglamide derivative and decreased dosages of chemotherapeutic agents may enable the treatment of patients in bad general condition that are not eligible for conventional chemotherapeutic treatment regimens due to the expected side effects. For some types of cancer that can already be cured chemotherapy in a majority of patients, the combination treatment of the present invention promises to reduce the required dosage of chemotherapeutic agents. Thus, in these cases a combination therapy may improve the quality of life for the patients without compromising the success of the treatment. A combination of TRAIL and Rocaglamide offers a potential treatment for currently incurable cancers such as human T-cell leukemia virus type 1 (HTLV-1)-associated adult T-cell leukemia/lymphoma (ATL). Hodgkin lymphoma (HL) of Hodgkin disease is a clonally related B-cell-derived malignancy. Although HL patients can be salvaged by using high-doses of multidrug therapy, one major drawback is late toxicity resulting from the therapy. Apparently, after 20 to 30 years, patients have a higher risk of dying from toxicities than from Hodgkin lymphoma (Re et al., Blood. 2005; 105:4553-60). As shown in example 3 and FIG. 7D rocaglamide sensitizes Hodgkin disease cells to TRAIL-mediated apoptosis. Thus, rocaglamide is useful for reducing the amount of other drugs in the therapy of Hodgkin disease thereby reducing the toxic side effects of said therapy.

In a further embodiment of the present innovation the combined preparation for simultaneous, separate or sequential use comprises at least one rocaglamide derivative and at least one agent which induces apoptosis in T-cells by activation induced cell death. This preparation is, preferably, used for the treatment of haematological cancers, more preferably for the treatment of T-cell leukaemia and T-cell lymphoma. It is based on the observation that a combination of a rocaglamide derivative and a T-cell receptor stimulating agent induces apoptosis in T-cell derived leukaemia cells, but not normal cells (see example 1).

Recently activated T-cells are resistant to apoptosis. The re-stimulation of pre-activated T-cells, in contrast, leads to activation-induced-cell-death (AICD). AICD is considered to be a protective mechanism that prevents autoimmunity. AICD is predominantly mediated by the CD95/CD95L system in T-cells. Malignant T-cells are susceptible to AICD, probably because they are similar to activated T-cells. CD95 is a so called death receptor. Its activation steers the cell towards apoptosis. CD95L is a ligand of CD95. Its binding to CD95 activates the extrinsic apoptotic pathway.

Rocaglamide derivatives increase the sensitivity of malignant T-cells for AICD by two mechanisms. (i) As set forth in the examples, rocaglamide derivatives increase the expression of CD95L in malignant T-cells cells, but not in normal T-cells. This increased expression of a ligand for a death receptor steers the cell towards apoptosis. (ii) Additionally, rocaglamide derivatives inhibit the expression of c-FLIP in malignant T-cells but not in normal T-cells. c-FLIP inhibits the activation of Caspase-8 and thus protects cells against apoptotic stimuli. The inhibition of c-FLIP expression by rocaglamide derivatives is mediated by the inhibition of NF-AT via over activation of the JNK signalling pathway.

The first murine anti-human CD38 chain monoclonal antibody (mAb) called OKT3, which targets CD3 of T-cell receptor in different T-cell clones regardless of antigen-specificity. OKT3, has been used for immune suppression in acute allograft rejection for more than two decades (Cosimi et al., 1981, Treatment of acute renal allograft rejection with OKT3 monoclonal antibody, *Transplantation* 32: 535-539; Ortho Multicenter Transplant Study Group, 1985, A randomized clinical trial of OKT3 monoclonal antibody for acute rejection of cadaveric renal transplants, *N Engl J Med* 313: 337-342). A humanized OKT3 mAb (hyOKT3 Ala-Ala) with less immunogenicity has been generated and several clinical studies showed clinical efficacy with better safety profiles (Herold et al., 2003, Activation of human T cells by FcR nonbinding anti-CD3 mAb, hOKT3gamma1 (Ala-Ala), *J Clin Invest* 111: 409-418; Woodle et al., 1999, Phase I trial of a humanized, Fc receptor nonbinding OKT3 antibody, huOKT3gamma1 (Ala-Ala) in the treatment of acute renal allograft rejection, *Transplantation* 68: 608-616). The hyOKT3 Ala-Ala anti-CD3 mAb could still induce detectable T cell activation in vitro and cytokine release in vivo (see Woodle et al., 1999; Popma et al., 2005, Anti-CD3 antibodies OKT3 and hOKT3gamma1(Ala-Ala) induce proliferation of T cells but impair expansion of alloreactive T cells; aspecifc T cell proliferation induced by anti-CD3 antibodies correlates with impaired expansion of alloreactive T cells, *Int Immunopharmacol* 5: 155-162).

Because rocaglamide derivatives act on the CD95/CD95L system which is a key mediator of AICD, AICD and rocaglamide derivatives synergistically enhance apoptosis in malignant T-cells. AICD in normal T-cells is significantly less enhanced by rocaglamide derivatives, because rocaglamide derivatives affect the expression of c-FLIP and CD95L in these cells only weakly.

Relating to the combination of at least one rocaglamide derivative and at least one T-cell receptor stimulating agent, the term "therapeutically effective amount" refers to the amounts of at least one rocaglamide derivative and the at least one agent which stimulates the T-cell receptor that are required to treat a haematologic cancer. It is known to the person skilled in the art that the therapeutically effective amount of a drug depends on the route of administration. If the rocaglamide derivative is injected, the therapeutically effective amount ranges, preferably, from 0.1 mg/kg to 300 mg/kg, more preferably from 0.1 mg/kg to 50 mg/kg body weight, most preferably from 0.1 mg/kg to 10 mg/kg.

The preferred therapeutic amounts for OKT3 range from 1 mg/kg to 10 mg/kg. Preferred therapeutic amounts for hyOKT3 Ala-Ala range from 10 µg/kg to 100 µg/kg.

The T-cell receptor is a molecule that is found on the surface of T-lymphocytes. It can recognize antigens that are bound to MHC-complexes (MHC: major histocompatibility complex) on other cells surfaces. It is a heterodimer. Binding of an antigen to the T-cell receptor activates the T-cell. Activation of a T-cell most importantly results in proliferation of said cell.

It is envisaged that the subject to be treated with a combination of at least one rocaglamide derivative and at least one T-cell receptor stimulating agent shall suffer from a haematological cancer, preferably from a T-cell derived haematological cancer. Preferably, the subject to be treated is a mammal, more preferably it is a rodent or a primate, most preferably it is a human.

Advantageously, the combined preparation comprising at least one rocaglamide derivative and at least one T-cell receptor stimulating agent offers alternatives to conventional chemotherapeutic agents for the treatment of haematological cancers. Rocaglamide derivatives specifically sensitize malignant T-cells to apoptotic stimuli by increasing their expression of CD95L and decreasing their expression of c-FLIP. The combination of a rocglamide derivative and an agent that stimulates the T-cell receptor has thus the potential to induce apoptosis selectively in malignant T-cells. Because rocaglamide derivatives do not sensitize normal T-cells to apoptotic stimuli to a significant degree, the combination treatment is highly specific. Hence, severe side effects do not have to be feared. Rocaglamide derivatives or T-cell stimulation alone are much less efficient against cancer as can be seen from the examples. Mice with xenografted tumors that were treated with a rocaglamide derivative or with T-cell stimulation alone still displayed tumor growth, although more slowly than untreated animals. Mice treated with the combination according to the present invention, in contrast, displayed a size reduction of the grafted tumors. Thus, the combination of the present invention has the potential to increase the anti-cancer activity of rocaglamide derivatives as compared to the monotherapy that is already known in the art.

In a further embodiment of the present invention at least one rocaglamide derivative is used for the manufacture of a medicament for the treatment of cancer in combination with at least one chemotherapeutic or antiproliferative agent. Preferably, at least one rocaglamide derivative and the at least one chemotherapeutic or antiproliferative agent are admixed into one pharmaceutical composition. Preferably, this composition additionally contains at least one pharmaceutically acceptable carrier. The at least one rocaglamide derivative may be employed in said composition in pure form or, where such forms exist, in pharmaceutically acceptable salt, ester or prodrug forms.

As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, phosphate buffer solutions; non-toxic, compatible lubricants such as sodium lauryl sulfate and magnesium stearate; as well as coloring agents, releasing agents, coating agents, sweetening, flavoring and perfuming agents. Preservatives and antioxidants can also be present in the composition, according to the judgment of the formulator.

The compositions may be administered to humans and other animals orally, rectally, parenterally, intracisternally, intravaginally, intraperitoneally, topically (as by powders, ointments, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion.

Dosage forms for topical or transdermal administration of rocaglamide derivatives include ointments, pastes, creams, lotions, gels, plasters, cataplasms, powders, solutions, sprays, inhalants or patches. The active component, i.e. the rocaglamide derivative, is admixed under sterile conditions with a pharmaceutically acceptable carrier and any needed preservatives or buffers as may be required. The ointments, pastes, creams and gels may contain, in addition to an active rocaglamide derivative of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to rocaglamide derivatives, excipients such as lactose, talc, silicic acid, aluminum hydroxide, calcium silicates and polyamide powder, or mixtures of these substances. Sprays can additionally contain customary propellants such as chlorofluorohydrocarbons. For nasal administration, rocaglamide derivatives will suitably be administered in liquid or powdered form from a nasal applicator. Forms suitable for ophthalmic use will include lotions, tinctures, gels, ointment and ophthalmic inserts, again as known in the art. For rectal administration, i.e., for topical therapy of the colon, rocaglamide derivatives may be administered in suppository or enema form, in particular in solution, e.g., in vegetable oil or like oily system for use as a retention enema.

Finally, the present invention relates to a method for the treatment of cancer administering the above described combined preparation to a patient.

All reference cited in this specification are herewith incorporated by reference with respect to their entire disclosure content and the disclosure content specifically mentioned in this specification.

The following examples are given to illustrate the present invention. It should be understood, however, that the spirit and scope of the invention is not to be limited to the specific conditions or details described in these examples but should only be limited by the scope of the claims that follow.

FIGURES

FIG. 1.

Roc sensitizes malignant T cells towards activation-induced cell death.

A. Chemical structures of Roc-A and Roc-Q. B. Roc-A sensitizes αCD3- or PMA/ionomycin-induced apoptosis in human leukemic Jurkat T cells. C. Roc-A sensitizes PMA/ionomycin-induced apoptosis in human leukemic DND-41 T cells, which contain a p53 mutation. D. Roc-A enhances T-cell-activation induced cleavages of caspase-8, -9, -3, and Bid in Jurkat T cells. Jurkat T cells were un-stimulated (−) or stimulated with PMA/ionomycin (+) in the absence or the presence of different dose of Roc-A for 24 h. Cell lysates were subjected to Western blot with antibodies against caspase-8, 9, 3, Bid, PARP, and control antibody against tubulin, sequentially. E. The anti-CD95L antibody NOK1 down-regulates Roc-A-mediated sensitization of cell death in Jurkat T cells. Jurkat T cells were treated with PMA/ionomycin and Roc-A in the absence or the presence of NOK1 for 30 h. F. Roc-A increases □APO-1 or LZ-CD95L induced apoptosis. Jurkat T cells were treated with □APO-1 or LZ-CD95L in the absence or the presence of 50 nM Roc-A for 24 h.

FIG. 2.

Roc does not sensitize normal T cells towards activation-induced cell death.

A. Roc does not sensitize freshly isolated normal T cells towards activation-induced cell death. Freshly isolated peripheral T cells (Day 0 T cells) were stimulated with PMA/ionomycin in the absence or the presence of Roc-A (50 nM) for 48 h. Apoptosis was determined as percentage of DNA fragmentation. B. Roc-A (50 nM) also does not sensitize pre-activated normal T cells towards activation-induced cell death. Freshly isolated T cells were stimulated with PHA and further cultured for 6 days (day 6 T cells) as described in materials and methods. The day 6 T cells were then re-stimulated with PMA/ionomycin in the absence or the presence of Roc-A. The apoptosis assays were carried out as described in A.

FIG. 3.

Roc-A sensitizes activation-induced apoptosis in mouse leukemic RMA T cells.

A. Roc-A sensitizes PMA/ionomycin-induced apoptosis in RMA T cells. RMA mouse leukemic T cells were treated with Roc-A in the absence or the presence of PMA/ionomycin. Apoptotic cells were determined after 24 h treatment. B. Roc-A and Roc-Q sensitizes ConA-stimulation induced cell death. Mouse RMA cells were stimulated with ConA in the presence or the absence of Roc-A or Roc-Q. Apoptosis was determined 16 h after treatment. C. Roc-mediated increase in activation-induced cells can be partially blocked by the anti-mouse FAS ligand antibody. The RMA cells were treated as in A in the absence or the presence of the anti-mouse FAS ligand antibody MFL-3. Surviving cells were determined after 24 h treatment by FSC/SSC FACS analysis.

FIG. 4.

Evaluation of the effect of Roc on activation-induced cell death in leukemic T cells in vivo.

A. Schematic descriptions of the first mouse experiment. Twenty C57/BL6 mice were implanted subcutaneously in the right dorsal flank region with RMA ($1\times10^6$ cells). One day after grafting, the mice were randomly separated into 4 groups and were treated with or without Roc-Q (1 mg/kg), Con A (5 mg/kg) or a combination of both by intraperitoneal injection (i.p.) as indicated. Tumor size was measured 8 days after implantation. B. Tumor volumes of mice untreated, treated with Roc-Q or Con A only, or a combination of both. Each symbol represents an individual mouse. C. Comparison of the tumor volumes of different groups of mice at the final day. D. Schematic description of the second mouse experiment. Twenty C57/BL6 mice were implanted subcutaneously in the right dorsal flank region with RMA ($2.5\times10^5$ cells). One day after grafting, the mice were randomly separated into 4 groups and were treated with or without Roc-Q (2.5 mg/kg), ConA (5 mg/kg) or a combination of both as indicated. Tumor size was measured after 9 days of implantation. At day 17, mice were killed and the tumor mass was weighed. E. Tumor volumes of mice untreated, treated with Roc-Q or ConA only, or with a combination of both. Each symbol represents an individual mouse. F. Comparison of the tumor weight of different groups of mice at the final day. G. GPT activities from blood of normal (no RMA grafting) and RMA-grafted mice untreated, treated with Roc-Q or ConA only, or with a combination of both. GPT levels below 50 U/l are in the normal range.

FIG. 5.

Effect of rocaglamide in combination with different anti-cancer agents on different cancer cell lines.

FIG. 6

Roc-AR sensitizes HTLV-1-associated ATL but not healthy T cells towards CD95L- and TRAIL-induced apoptosis.

A. Roc-AR sensitizes HTLV-1-associated ATL cells towards CD95L- and TRAIL-induced apoptosis. The HTLV-1-associated ATL cell lines SP, MT-2, ATL-3 and CHAMP were left untreated or treated either with Roc-AR (100 nM), LZ-CD95L (100 ng/ml) or Superkiller-TRAIL (100 ng/ml) alone or in combination for 16 h. Apoptotic cell death was determined as DNA fragmentation. The results shown are representative of three independent experiments. B. Roc-AR does not sensitize healthy T cells towards CD95L- and TRAIL-induced apoptosis. Freshly isolated peripheral blood T cells from three healthy donors were left untreated or treated with Roc-AR, LZ-CD95L or Superkiller-TRAIL alone or in combination as in A for 16 h. SP cells were used as a positive control. Apoptotic cell death was determined as DNA fragmentation. Results are representative of three independent experiments. C. Roc-AR enhances CD95L- and TRAIL-induced pro-casp-8 processing. SP and MT-2 cells were left untreated or treated with indicated drugs either alone or in combination as in A for 4 h. Cell lysates were subjected for Western blot analysis by antibodies against caspase-8 and 3 as indicated. Equal protein loading was controlled by tubulin.

FIG. 7.

Roc-AR overcomes TRAIL-resistance in Hodgkin lymphoma cells.

A. Hodgkin lymphoma cells were resistant to TRAIL. Hodgkin lymphoma cell lines L1236 and KM-H2 were treated with different concentrations of TRAIL for 48 h. Jurkat cells were used as a positive control. Apoptotic cell death was determined by DNA fragmentation. B. Hodgkin lymphoma cells express elevated levels of c-FLIP and cyclin D. Total cell lysates from Jurkat, L1236 and MK-H2 cells were analyzed by Western blot with antibodies against c-FLIP, XIAP, cyclin D1 and D2. Equal loading of proteins were controlled by tubulin. C. Roc-AR inhibits ERK activity and down-regulates c-FLIP, cyclin D1 and D2 expression in L1236 and KM-H2 cells. L1236 and KM-H2 cells were treated with 50 or 100 nM Roc-AR for indicated times. Total cell lysates were subjected to Western blot by indicated antibodies. D. Roc-AR cooperates with XIAP inhibitor (13098#) to enhance apoptosis induction in L1236 and KM-H2 cells. KM-H2 cells were treated for 48 h with either Roc-AR (50 nM), 13098# (5 µM) and TRAIL (50 ng/ml) alone or in combinations as indicated. Apoptotic cell death was determined by DNA fragmentation. Results represent data of two independent experiments.

FIG. 8.

HTLV-1-associated ATL cells are resistant to TRAIL and express higher levels of c-FLIP.

A. HTLV-1-associated ATL cell lines are characterized by express the viral protein Tax. HTLV-1-infected ATL cell lines SP, MT-2, CHAMP and ATL-3 and non-infected cell lines Jurkat and CEM were subjected to Western blot with antibody against Tax. B. HTLV-1-infected ATL cell lines are resistant to TRAIL-induced apoptosis. CEM, Jurkat, and the HTLV-1-infected ATL cell lines were treated with different concentration of TRAIL. Apoptotic cell death was determined by DNA fragmentation. C. All HTLV-1-infected ATL cell lines express TRAIL receptor 1 and 2. D. All HTLV-1-infected cell lines express elevated c-FLIP proteins. Total cell lysates from HTLV-1-infected and non-infected cell lines were analyzed for c-FLIP expression by Western blot.

EXAMPLE 1

Rocaglamide Sensitizes Leukemic T Cells Towards CD95/CD95L-Mediated Apoptosis by Differential Regulation of CD95L and c-FLIP Expression Materials and Methods Cell Lines and Culture The mouse lymphoma cell line RMA (van Hall et al., 2000), the human leukemic T cell lines DND-41 (contains a p53 mutation), Jurkat J16, Jurkat A3 and Jurkat A3 deficient in FADD (J-FADDdef) (purchased from American Type Culture Collection, ATCC, Manassas, USA) were cultured in RPMI 1640 medium (GIBCO laboratories, Grand Island, N.Y.) supplemented with 10% FCS, 50 µg/ml gentamicin (GIBCO), 6 mM HEPES (GIBCO, 1 M solution), and 2 mM L-glutamine (GIBCO, 200 mM solution) at 37° C. and 5% $CO_2$. T cells were stimulated with either plate-bound αCD3 (OKT3 10 µg/ml) or PMA (5 ng/ml) plus ionomycin (0.5 µM).

Preparation of Human T Cells from Peripheral Blood

Human peripheral T cells were prepared as described previously (Klas et al., 1993) and were more than 90% CD3 positive. For activation, resting T cells (day 0) were cultured at 2×106 cells/ml with 1 µg/ml PHA for 16 h (day 1). Day 1 T cells were then washed three times and cultured for an additional 5 days in the presence of 25 U/ml IL-2 (day 6).

Determination of Apoptosis

Cells were plated in triplicates and treated for the indicated periods of time at 37° C. with different reagents as described in the figure legends. Rocaglamide derivatives used in this study were isolated from various Aglaia species to at least 98% purity determined by HPLC as reported previously (Schneider et al., 2000). The structures of the compounds were unequivocally elucidated based on their NMR and mass spectra as described before (Schneider et al., 2000). Apoptotic cell death was examined by two parameters: FSC/SSC index of apoptotic-like change in cell size and granularity by FACScan and by analysis of DNA fragmentation (Vermes et al., 2000).

Western Blot Analysis

1×106 cells were sedimented and lysed for 15 min in ice-cold lyses buffer (29 mM Tris-HCl, pH 7.4, 137 mM NaCl, 10% (w/v) Glycerin, 1% (v/v) Triton X-100, 2 mM EDTA, 1 mM PMSF, 0.4 mM NaVa4, 10 mM NaF, complete protease inhibitor cocktail, Roche). After removing the cell debris by centrifugation at 13,000 rpm for 15 min, equal amounts of proteins were separated on a 12% SDS-PAGE, blotted onto a nitrocellulose membrane (Amersham Biosciences, Little Chalfon, UK) and blocked with 5% non-fat drymilk in PBS/Tween (0.05% Tween-20 in PBS). The following antibodies were used: Caspase-9 mAb (Santa Cruz Biotechnology, Santa Cruz, Calif.), The caspase-8 mAb C15 (mouse IgG2b) recognizes the p18 subunit of caspase-8, the c-FLIP mAb NF6, the agonistic anti-CD95 mAb, anti-APO-1, and LZ-CD95L were generated in our lab and described previously (Scaffidi et al., 1997; Trauth et al., 1989; Walczak et al., 1999). caspase-3 polyclonal antibody (Cell Signalling, Inc. Beverly, Mass.), anti-Tubulin (Sigma, Taufkirchen, Germany), Bid polyclonal antibody (Biosource International, Nivelles, Belgium), Bid polyclonal antibody recognizes cleaved Bid (Cell Signalling), anti-JNK1 (C-17) (Santa Cruz), anti-phospho-JNK antibody (Cell Signaling), actin and tubulin (Sigma), IκBα (C21, sc-371) (Santa Cruz, Calif.); the anti-c-Jun mAb (BD-Bioscience-Phamingen, Belgium) and the anti-phospho-c-Jun (Ser63) antibody (Cell Signaling). For stripping, blots were incubated for 30 min in a buffer containing 62.5 mM Tris/HCl, pH 6.8, 2% SDS, and 100 mM β-mercaptoethanol at 56° C. The blots were washed six times for 10 min in PBS/Tween and blocked again in 5% non-fat drymilk.

Quantitative Real-Time PCR

TaqMan quantitative real-time PCR has previously been described in detail (Heid et al., 1996). The sequence for primers of CD95L, c-FLIPL, c-FLIPS, β-actin and fluorescent-labelled probes used in these studies was described previously (Li-Weber et al., 2002; Krueger et al., 2006). PCR was performed in a 12.5 µl reaction mixture (PCR kit from Eurogentech, Belgium) that contained 0.08 µg of reverse transcribed cDNA and proper amounts of primers and probe. For each sample three PCR reactions were performed. The resulting relative increase in reporter fluorescent dye emission was monitored by the TaqMan-system (GeneAmp 5700 sequence detection system and software, Perkin Elmer, Foster City, Calif.). The mRNA levels of the target genes, relative to β-actin, was calculated using the formula: Relative mRNA expression=2−(Ct of cytokine−Ct of β-actin) where Ct is on the threshold cycle value.

Plasmid Constructs and Transient Transfections

The luciferase reporter construct containing multiple copies of the AP-1 binding site from SV40 enhancer (CGGTTGCTGACTAATTG) was described previously (Li-Weber et al., 1999). Jurkat T cells were transfected by electroporation as previously described (Li-Weber et al., 1999). After overnight recovering, the cells were divided and stimulated with PMA (5 ng/ml) and ionomycin (0.5 µM) in the absence or presence of Roc for 8 h. Luciferase activity was determined in 10 µl of cell extract using the luciferase assay substrate (Promega Corp., Heidelberg, Germany) with a Duolumat LB9507 luminometer (Berthold, Bad Wildbad, Germany).

In Vivo Mouse Studies

C57/BL6 mice were implanted subcutaneously in the right dorsal flank region with RMA ($1 \times 10^6$ cells). One day after grafting, Roc-Q (1 mg/kg body weight, dissolved in DMSO and diluted in olive oil) was administered by intraperitoneal injection (i.p.) as indicated in the figure legend. The control group was treated in an analogous manner with the vehicle. The tumor size was measured with a micrometer caliper at the indicated times and the tumor volume (V) was calculated by the formula $V=(a^2 \times b)/2$, where "a" is the width and "b" is the length in mm (Mattern et al., 1998). All protocols using and maintaining animals were approved by the German Animal Protection Authority (Office Regierungspräsidium Karlsruhe). Treated and control animals were compared for differences in tumor growth after end of treatment using the non-parametric method in a one-sided statistical test at the significance level of 0.05 (Koziol et al., 1981).

Quantitative Determination of Glutamate Pyruvate Transaminase (GPT)

To examine the liver toxicity of Rocaglamide, the activities of GPT were determined from the heparinized blood of mice by test strips Reflotron® GPT as described by the instruction of the manufacture (Roche 10745138). The normal levels of GPT activity should be below 50 U/l.

Results

Roc Sensitizes Malignant T Cells Towards CD95/CD95L-Mediated Apoptosis

Two Roc derivatives, Roc-A and Roc-Q, were used in this study (FIG. 1A). To investigate the effects of Roc on CD95/CD95L-mediated apoptosis in malignant T cells, the human leukemic T-cell lines Jurkat and DND-41 (contains a p53 mutation) were stimulated with either αCD3 or PMA/ionomycin to induce CD95L expression in the absence or the presence of different concentrations of Roc-A. In the absence of Roc-A, approximately 5 to 10% of Jurkat T cells underwent apoptosis after 24 h stimulation by PMA/ionomycin or by αCD3. Roc-A alone also induced about 5 to 10% of apoptotic cell death in Jurkat T cells. Noticeably, stimulation of Jurkat T cells in the presence of Roc-A resulted in a dose-dependent increase in apoptotic cell death (FIG. 1B). Compared to Jurkat T cells, DND-41 T cells were more resistant to Roc-A- or T-cell-stimulation-induced cell death. However, a dramatic increase in apoptotic cell death was observed when DND-41 T cells were treated with the combination of Roc-A and PMA/ionomycin stimulation (FIG. 1C). Similar results were also observed in other human leukemia T cell lines, e.g. Molt-4 and Hut78 (data not shown). The ability that Roc-A could increase activation-induced-cell-death was confirmed by Western blot analysis of important proteins involved in the apoptotic pathways (FIG. 1D). As shown in FIG. 1D, T-cell stimulation alone led to only a weak activation of caspase-8, the main caspase involved in the extrinsic pathway, and did not activate caspase-9, the main caspase involved in the intrinsic (mitochondrial) pathway in Jurkat T cells. Due to the week activation of caspase-8, T-cell stimulation alone generated very little or almost no detectable amounts of the active caspase-3 cleavage product p17 (although the p19 caspase-3 cleavage products were generated) (FIG. 1D). Treatment with Roc-A alone led to activation of caspase-9 and generation of a detectable amount of the active p17 caspase-3 product and weak PARP cleavage. However, combinations of Roc-A with T-cell stimulation, in contrast, strongly increased cleavages of caspase-8 (FIG. 1D). Enhanced caspase-8 activity correlates with complete cleavage of Bid and consequently enhances cleavage of caspas-9, -3 and PARP (FIG. 1D).

To confirm that the Roc-A-mediated increase in cell death involves the CD95/CD95L system, we carried out an experiment with the anti-CD95L antibody NOK1. The experiment showed that at least 50% of the Roc-A-increased apoptosis was blocked by NOK1 (FIG. 1E). Furthermore, enhanced apoptotic cell death could be also obtained by treating Jurkat cells with combinations of Roc-A with the anti-CD95 antibody (αAPO-1) or with the recombinant LZ-CD95L protein (FIG. 1F). Theses experiments demonstrate that Roc can sensitize CD95/CD95L-mediated apoptosis.

Roc does not Promote Activation-Induced Cell Death in Normal T Cells

Figure 2:
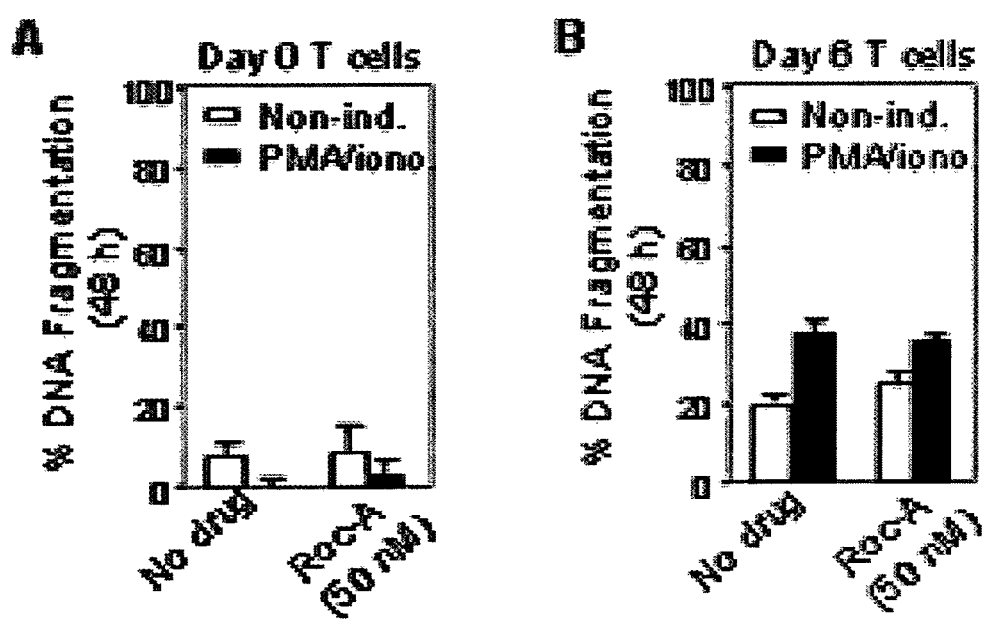

We have previously shown that Roc has no or very little toxicity on normal resting peripheral lymphocytes (Zhu et al., 2007). To investigate the effect of Roc on activated normal T cells, freshly isolated peripheral blood T cells (Day 0 T cells) were stimulated with PMA/ionomycin in the absence or the presence of Roc-A. Consistent with the previous study (Klas et al., 1993, Zhu et al., 2007), the day 0 (resting) T cells were resistant to PMA/ionomycin-induced cell death. Roc-A alone had no toxicity on day 0 T cells (FIG. 2A). Roc-A also did not increase cell death in combination with PMA/ionomycin stimulation in day 0 T cells (FIG. 2A). Freshly activated T cells are known to be resistant to activation-induced-cell-death whereas T cells activated for several days in culture become sensitive towards CD95/CD95L-mediated activation-induced-cell-death (Klas et al., 1993). Therefore, freshly isolated T cells were stimulated by PHA and further cultured for 6 days (day 6 T cells) and were then re-stimulated with PMA/ionomycin in the absence or the presence of Roc-A. Although day 6 T cells were more susceptible (about 50% more) to PMA/ionomycin-induced cell death compared to day 0 T cells, Roc-A did not further enhance PMA/ionomycin-induced cell death in these cells (FIG. 2B). These data show that Roc preferentially enhances activation-induced-cell-death in malignant T cells.

Figure 3:
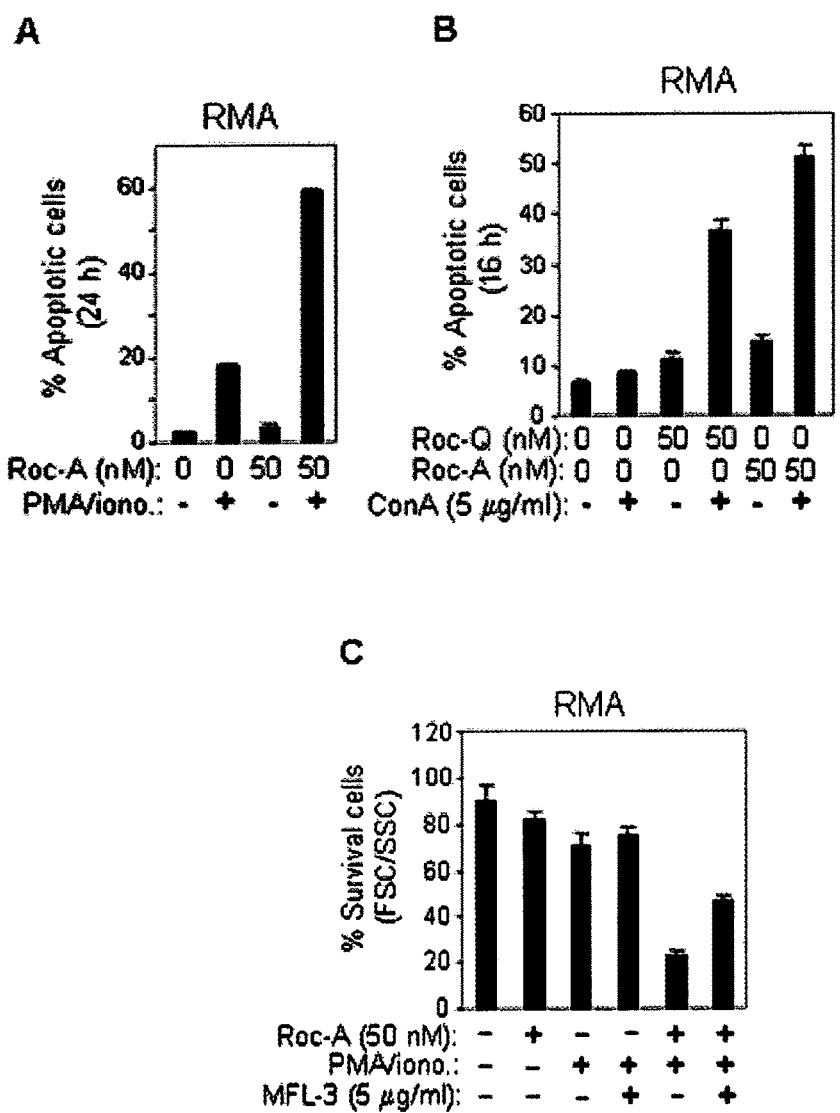

In Vivo Evaluation of the Effect of Roc on Activation-Induced Cell Death in Leukemic T Cells To explore the potential anti-tumor effect of Roc in vivo, we carried out an animal study using the mouse T lymphoma cell line RMA as a model system. Similar to human malignant T cells, Roc (Roc-A and Roc-Q) enhanced PMA/ionomycin- or Con A-stimulation induced cell death in RMA cells in vitro (FIG. 3A, B). The enhanced cell death could be largely inhibited by the anti-mouse CD95L antibody MFL-3, demonstrating that the CD95/CD95L system was involved (FIG. 3C).

Figure 4:
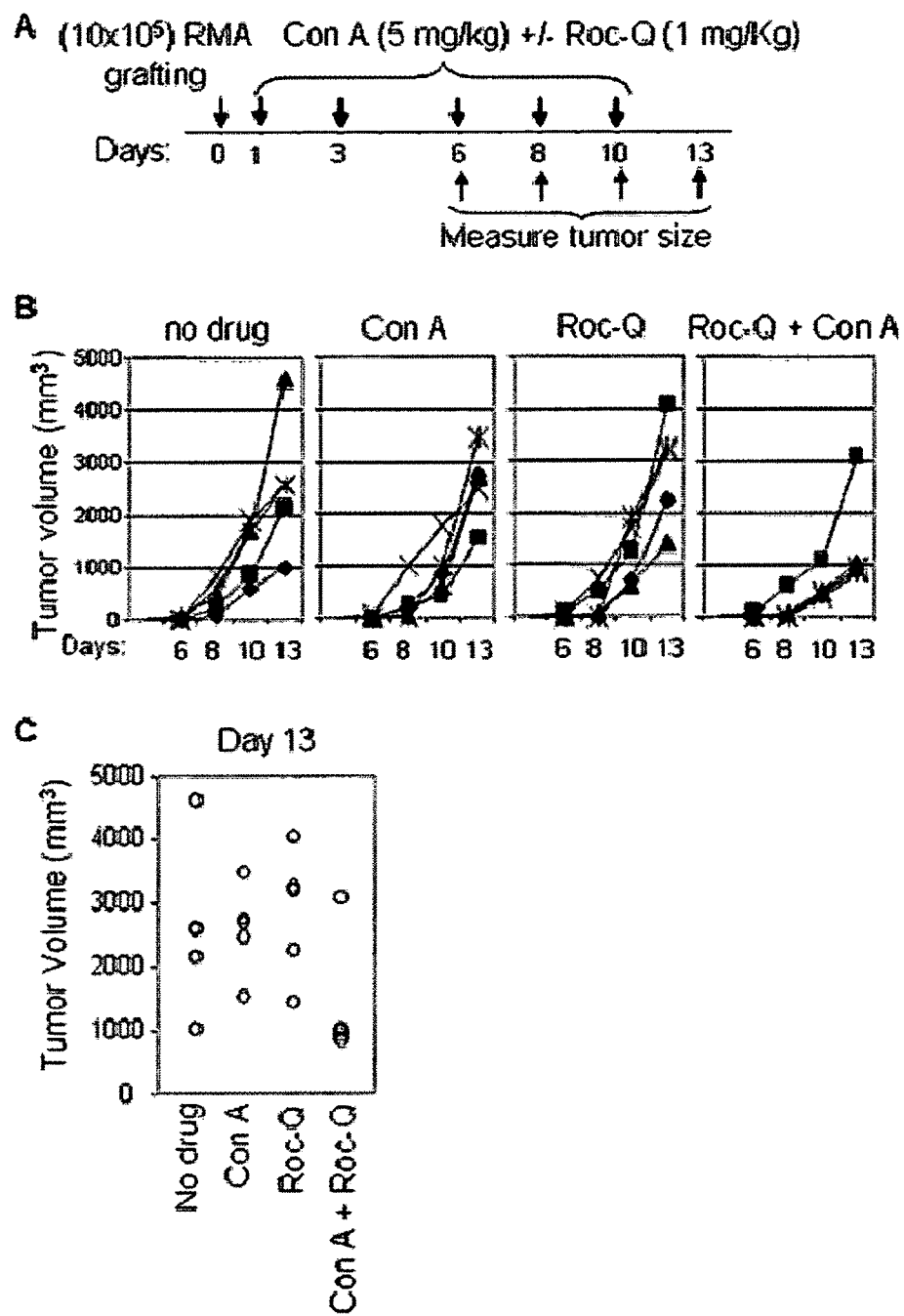
Figure 4:
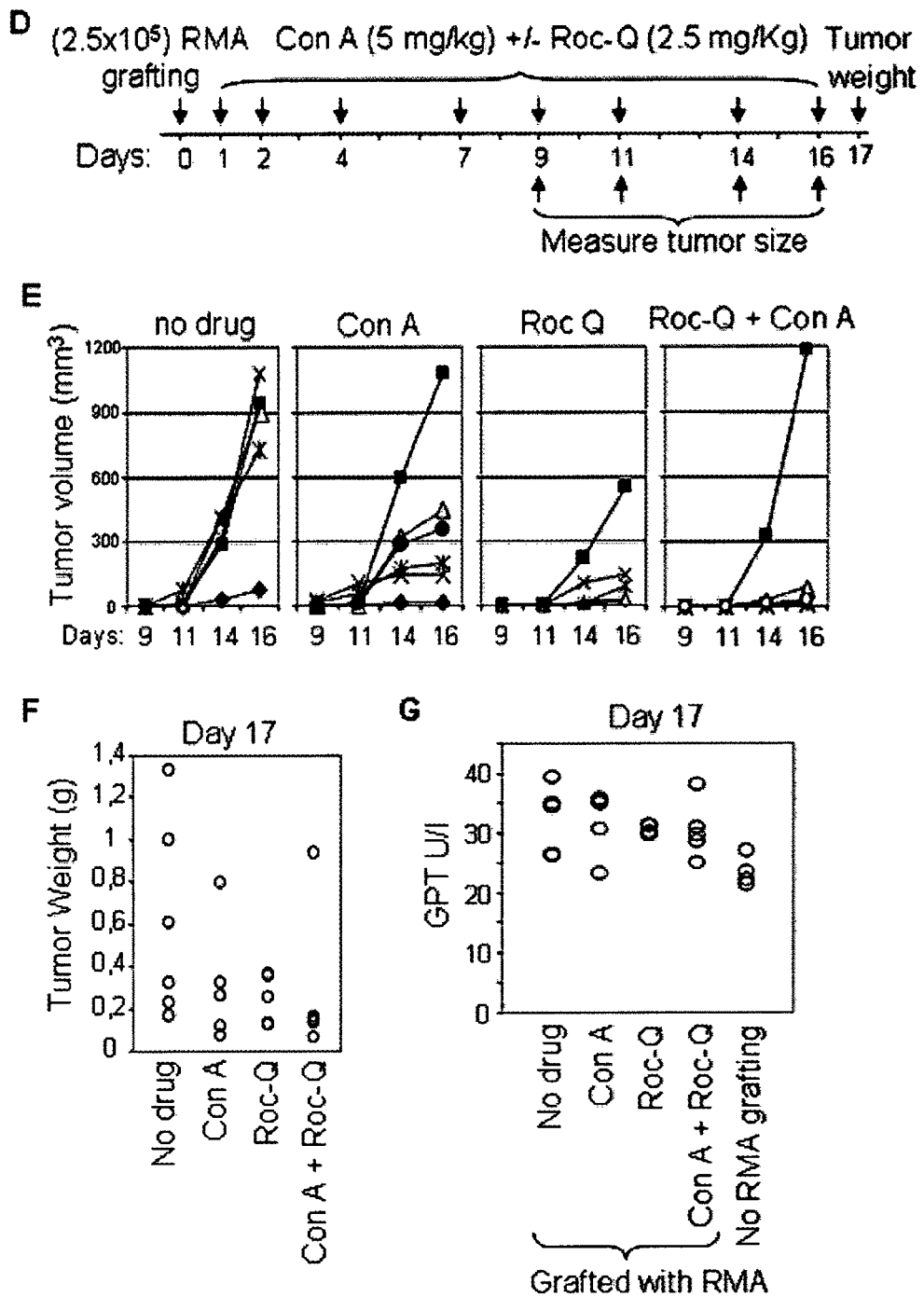
Figure 5A:
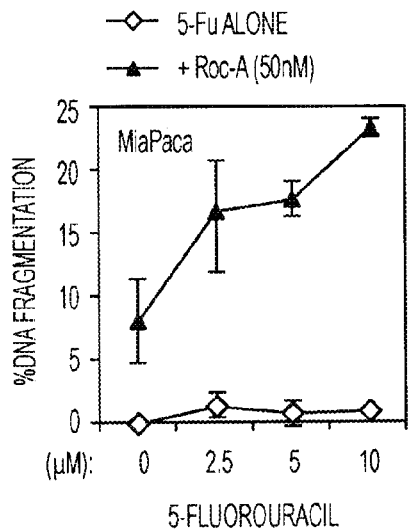
Figure 5B:
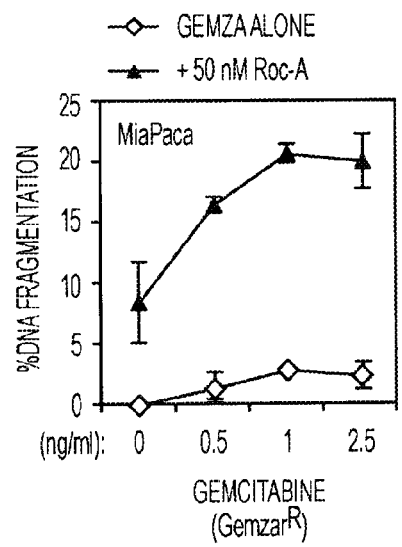
Figure 5C:
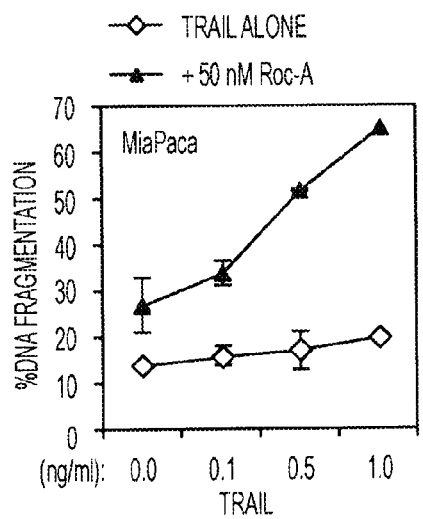
Figure 5D:
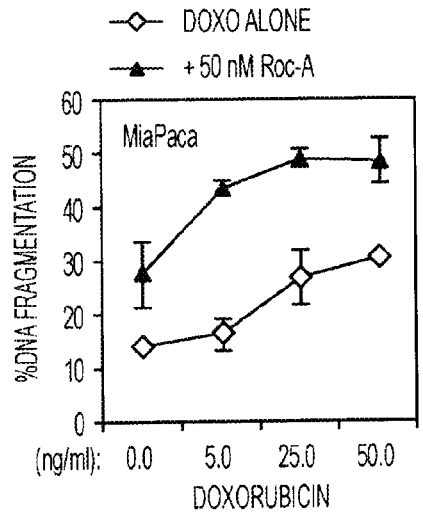
Figure 5E:
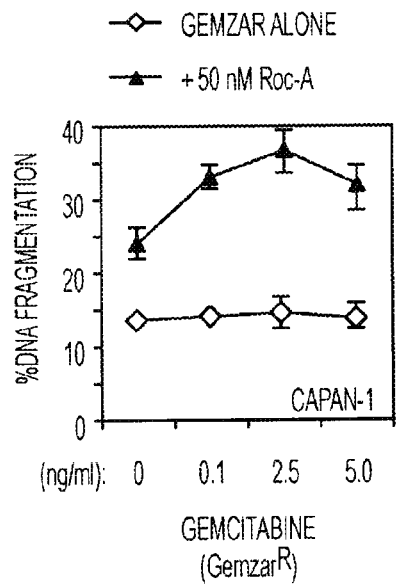
Figure 5F:
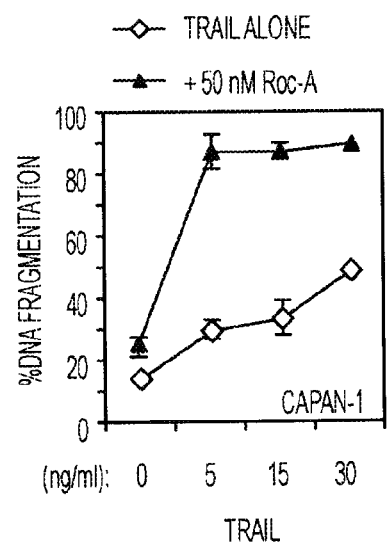
Figure 5G:
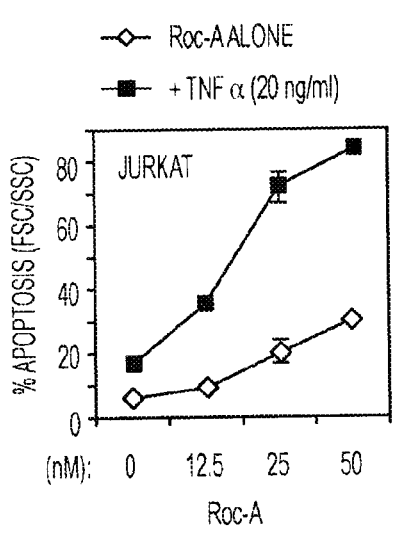
Figure 5H:
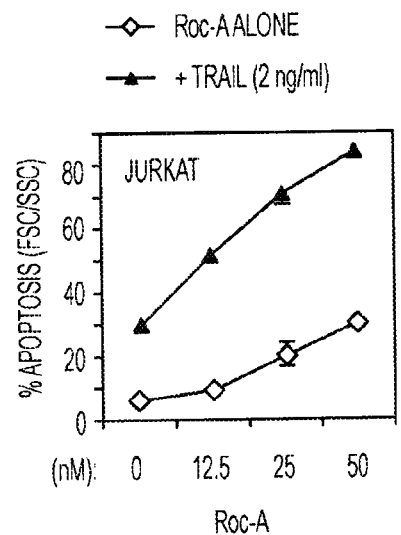

To investigate whether the effect of Roc on activation-induced cell death is also occurred in vivo, RMA cells were grafted subcutaneously into the C57/BL6 mice. One day after xenografting, the mice were randomly separated into four groups (each group contains 5 mice). One group with no treatment was taken as a control, and the other three groups received Con A, Roc-Q, or a combination of Roc-Q and Con A, respectively, three times per week by intraperitoneal injection (i.p.). Two independent experiments were carried out. In the first experiment, RMA ($10 \times 10^5$ cells)-grafted mice were treated with or without 1 mg/kg body weight of Roc-Q in the presence or absence of Con A as described in FIG. 4A. No toxicity was seen up to a dose of 10 mg/kg body weight (Lee et al., 1998). Acute toxicity was reported with an LD50 of >300 mg/kg (Umezawa et al., 1997). The experiment showed that the control mice developed tumors in 7 days after xenografting. No significant changes in tumor size and tumor growth rate were seen in mice treated with only Con A or only Roc-Q. However, delayed tumor growth (FIG. 4B) and reduced tumor sizes (FIG. 4C) were seen in mice treated with the combination of Roc-Q and Con-A. In order to obtain a clear view of the therapeutic effect, mice were grafted with a reduced amount of tumor cells ($2.5 \times 10^5$ RMA cells) and were then treated with an increased dose (2.5 mg/kg body weight) of Roc-Q as described in FIG. 4D. In this experiment, the control mice developed tumors after 9 days. Significantly delayed tumor growth was observed in mice which received only Roc-Q or only Con A (FIG. 4E). Combination treatment led to further inhibition (except for one mouse) of tumor progression (FIG. 4E) and tumor growth (FIG. 4F). One mouse in the combination treatment did not show the expected anti-tumor effect. Since all mice that were treated with Roc-Q alone showed reduced tumor sizes and tumor weight, we assume that this exception might be due to an improper delivery of the drugs. No liver toxicity (FIG. 4G) and no body weight loss were seen in mice after treatment.

EXAMPLE 2

Figure 8:
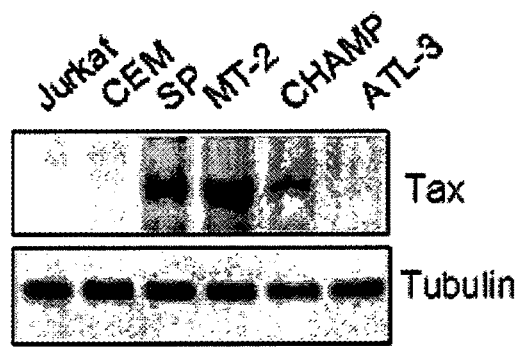
Figure 8:
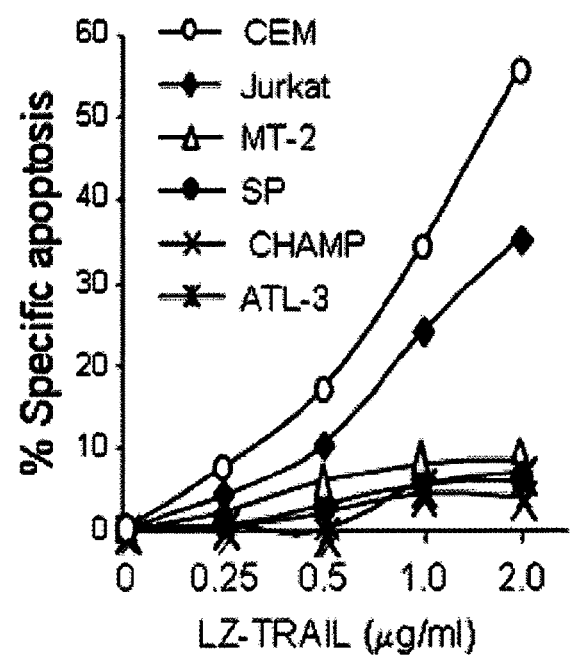
Figure 8:
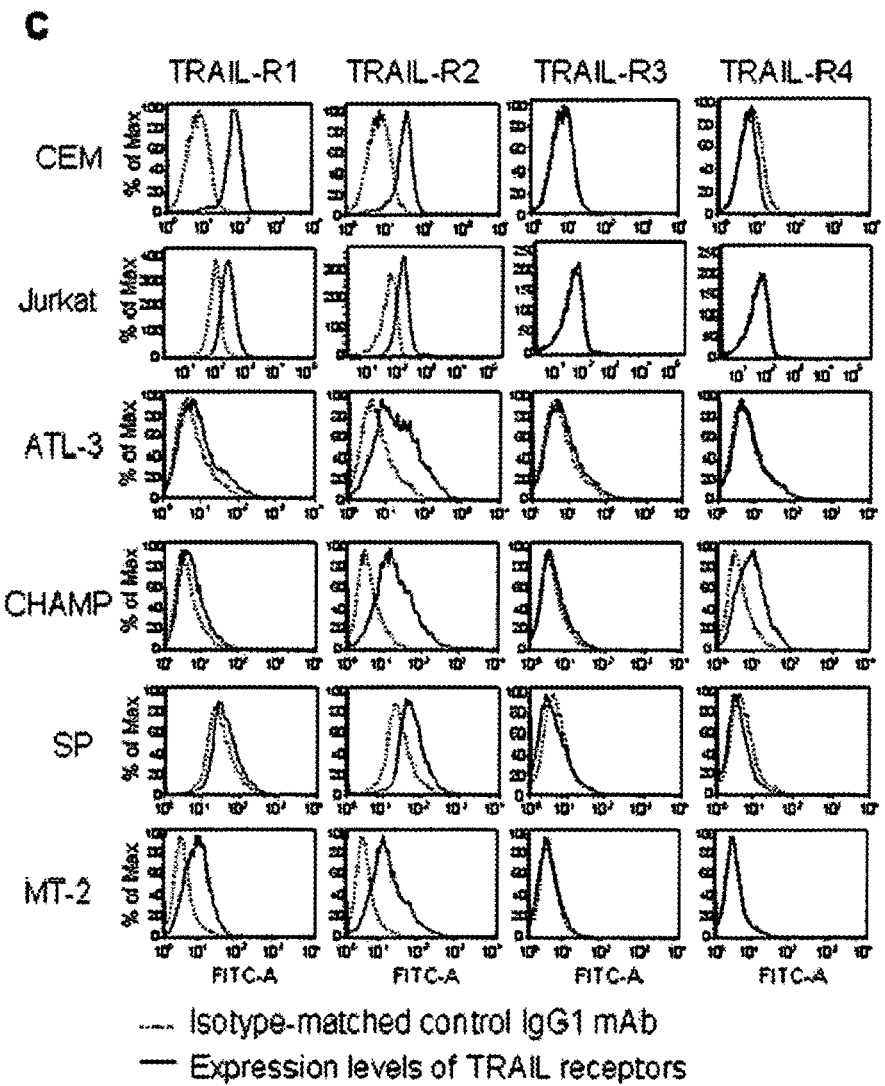
Figure 8:
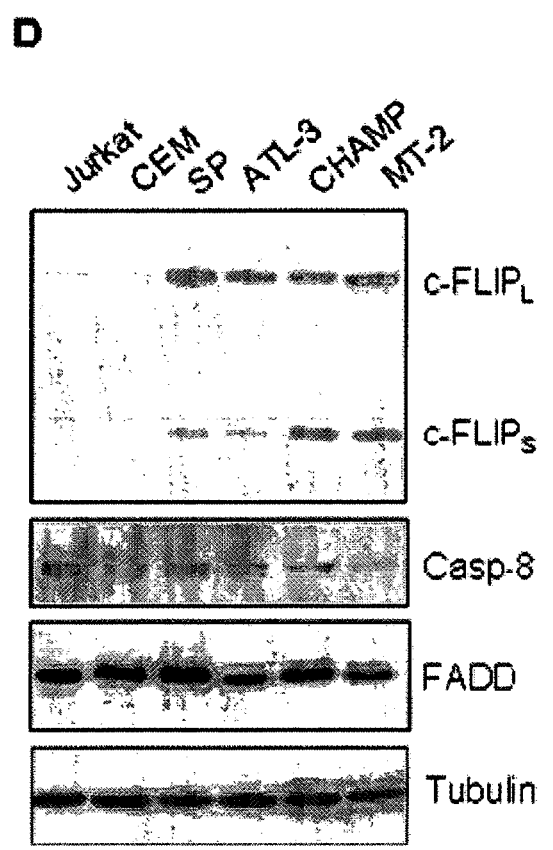

Effect of Rocaglamide in Combination with Different Anticancer Agents on Cancer Cell Lines Pancreatic carcinoma cell lines MiaPaca and Capan-1 were treated with Roc-A (50 nM) in combination with different doses of anticancer reagents for 48 h. Apoptotic cell death was determined by Nicoletti (DNA-fragmentation). The leukemia cell line Jurkat was treated with either TNFα (20 ng/ml) or TRAIL (2 ng/ml) in combination with different doses of rocaglamide as indicated for 24 h. Apoptotic cell death was determined by FSC/SSC. As shown in FIG. 8 the combination of rocaglamide and the anticancer agents synergistically increased the apoptic cell death.

EXAMPLE 3

Synergistic Effects of Roc-AR and TRAIL on Apoptosis of Leukaemia Cells In Vitro Cells and Cell Cultures The human malignant cell lines used in this study are: the human leukemic T cell lines CEM and Jurkat (J16), the HTLV-1 ATL derived cell lines SP, MT-2, CHAMP, and ATL-3, and Hodgkin lymphoma derived cell lines L1236 and KM-H2. Human peripheral blood T cells were prepared as described previously (Zhu et al., 2009) and were more than 90% CD3 positive. All cells were cultured in RPMI 1640 medium (GIBCO laboratories, Grand Island, N.Y.) supplemented with 10% FCS, 50 μg/ml gentamicin (GIBCO), 6 mM HEPES (GIBCO, 1 M solution), and 2 mM L-glutamine (GIBCO, 200 mM solution) at 37° C. and 5% $CO_2$.

Determination of Apoptosis

Cells were plated in triplicates and treated for the indicated periods of time at 37° C. with different doses of Rocaglamide AR (Roc-AR) (>98% pure, assessed by HPLC) (Proksch et al., 2005), Superkiller-TRAIL (Alexis) or LZ-CD95L (Walczak et al., 1999) alone, or in combinations as indicated in figures. Apoptotic cell death was determined by analysis of DNA fragmentation (% DNA fragmentation) as previously described (Krueger et al., 2006). Specific apoptosis was calculated as (percentage of experimental apoptosis–percentage of spontaneous apoptosis)/(100–percentage of spontaneous apoptosis)×100.

Figure 6:
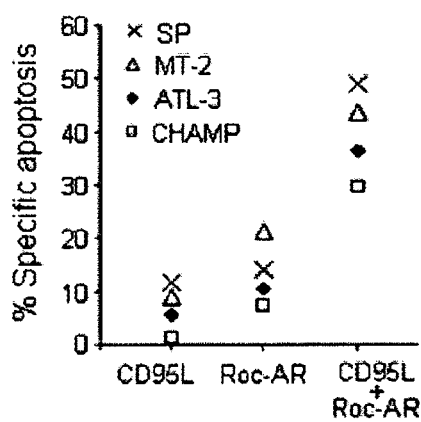
Figure 6:
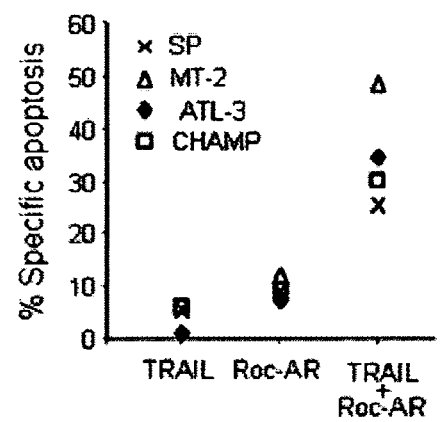
Figure 6:
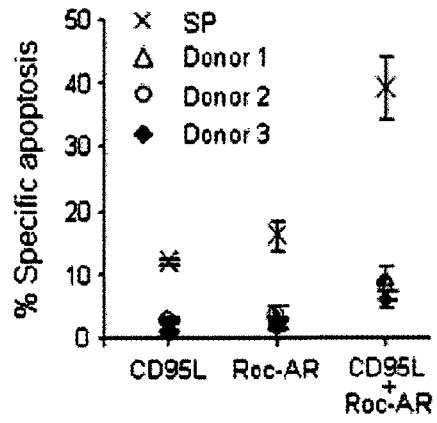
Figure 6:
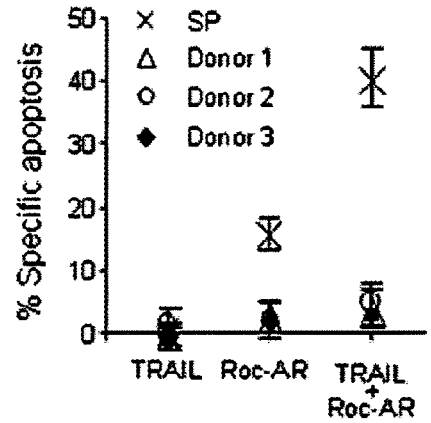
Figure 6:
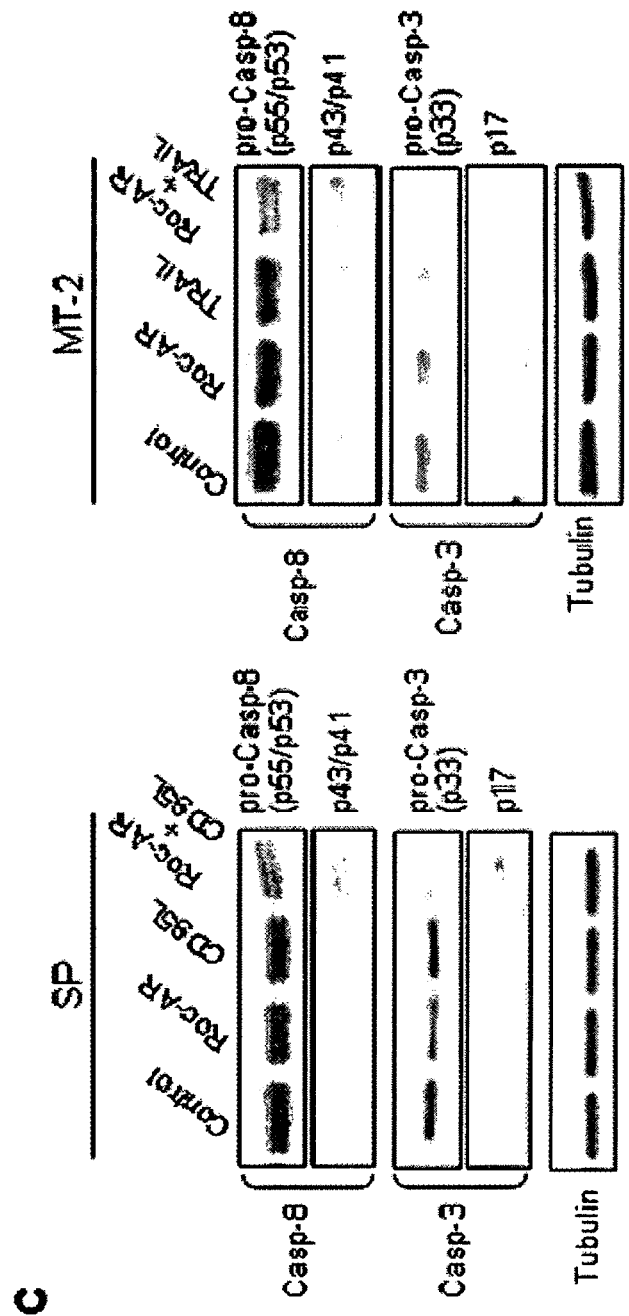

Roc Sensitizes CD95L- and TRAIL-Mediated Apoptosis in ATL but not in Normal T Cells Treatment of the ATL cells in the presence of Roc-AR significantly increased CD95L- and TRAIL-induced apoptotic cell death (FIG. 6A). In contrast, Roc-AR did not sensitize normal peripheral blood T cells to CD95L- and TRAIL-mediated apoptosis (FIG. 6B). The ability of Roc-AR to enhance receptor-mediated apoptosis was further demonstrated by Western blot showing that caspase-8 activity was enhanced by the combination treatment which could be observed as early as 4 h after treatment (FIG. 6C). The sensitization is not due to enhanced expression of receptors since Roc-AR treatment did not influence the cell surface expression levels of CD95 and TRAIL receptors. These data demonstrate that Roc can sensitize HTLV-1-infected leukemic cells towards CD95L- and TRAIL-mediated apoptosis by down-regulation of c-FLIP.

Roc Sensitizes TRAIL-Mediated Apoptosis in Hodgkin Lymphoma Cells

Figure 7:
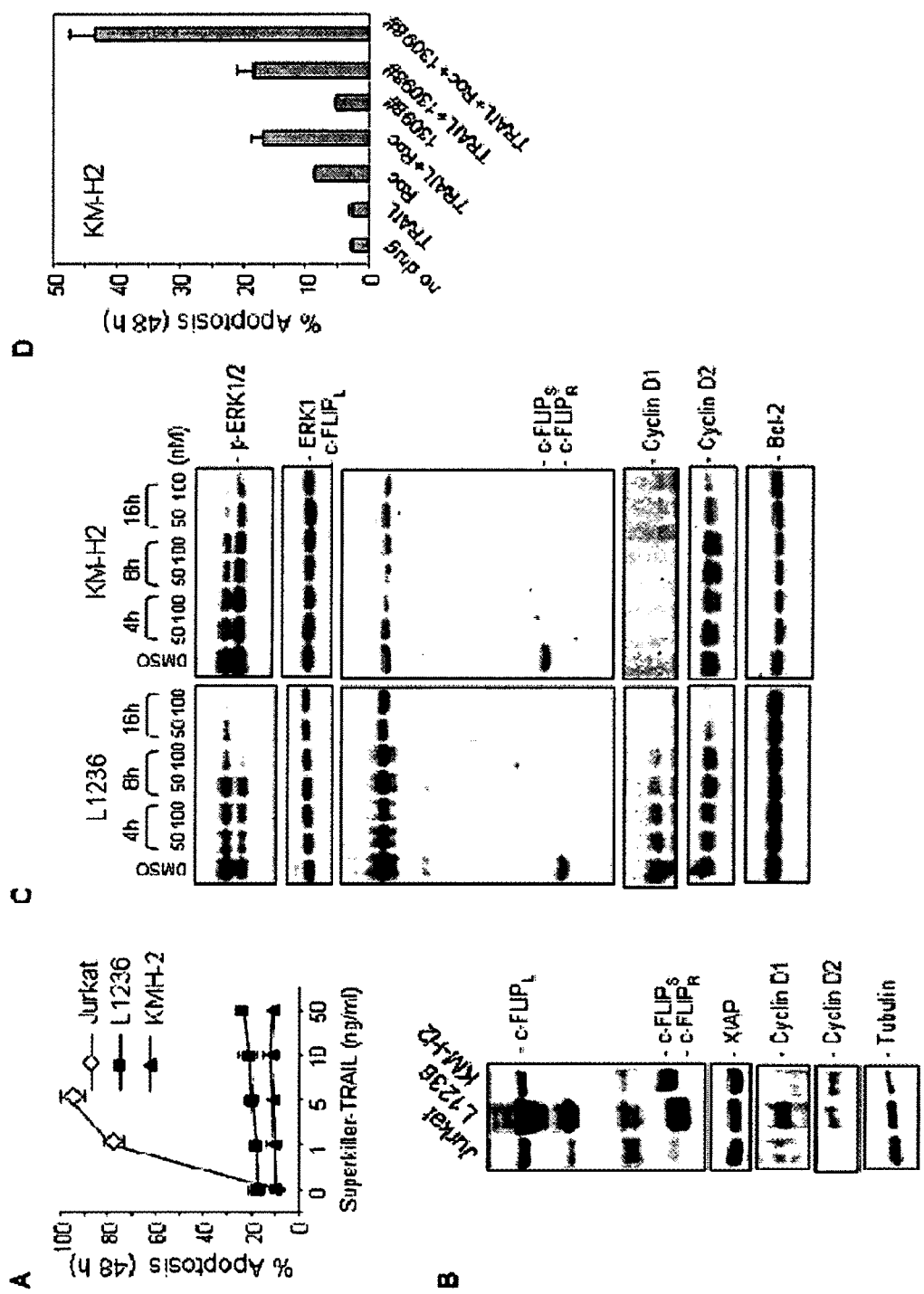

L1236 and KM-H2 cells were completely resistant to TRAIL-mediated apoptosis (FIG. 7A). Both cell lines were shown to express elevated levels of c-$FLIP_S$ and cyclin D2 compared to Jurkat cells (FIG. 7B). L1236 cells also overexpress cyclin D1 (FIG. 7B). Treatment of L1236 and KM-H2 with Roc-AR resulted in inhibition of ERK phosphorylation and down-regulation of c-FLIP, in particular c-$FLIP_S$, and cyclin D1 and D2 expression (FIG. 7C). Consequently, Roc-AR increase TRAIL-mediated apoptotic cell death and, particularly, synergistically enhanced TRAIL killing in combination with the XIAP inhibitor 13098# (FIG. 7D). These data further support that Roc may be a potential adjuvant for TRAIL-based anticancer therapy.

LITERATURE

Heid, C A., Stevens J, Livak K J, Williams P M. 1996. Real time quantitative PCR. Genome Res. 6:986.
Klas C, Debatin K M, Jonker R P, Krammer P H. Activation interferes with the APO-1 pathway in mature human T cells. Int Immunol. 1993; 5:625-630.

Koziol J A., Maxwell D A., Fukushima M, Colmerauer M E, Pilch Y H. A distribution free test for tumor-growth curve analyses with application to an animal tumor immunotherapy experiment. Biometrics. 1981; 37:383-390.
Li-Weber, M., Laur, O. and Krammer, P H. Novel Egr/NF-AT composite sites mediate activation of the CD95 (APO-1/Fas) ligand promoter in response to T-cell stimulation. Eur. J. Immunol., 1999; 29:3017-3027.
Li-Weber, M., Weigand, M., Giaisi, M., Süss, D., Treiber, M., Baumann, S., Ritsou, E., Breitkreutz, R. and Krammer, P H. Vitamin E inhibits CD95 ligand expression and protects T cells from activation-induced-cell-death. J. Clin. Invest., 2002; 110:681-690.
Mattern J, Bak M, Hahn E W, Volm M. Human tumor xenografts as model for drug testing. Cancer Metastasis Rev. 1998; 7:263-284.
Proksch, P., Giaisi, M., Treiber, M. K., Palfi, K., Merling, A., Spring, H., Krammer, P. H., Li-Weber, M. Rocaglamide derivatives are immunosuppressive phytochemicals that target NF-AT activation in T cells. J. Immunol., 2005; 174:7075-708.
Scaffidi C, Medema J P, Krammer P H, Peter M E. FLICE is predominantly expressed as two functionally active isoforms, caspase-8/a and caspase-8/b. J Biol Chem 1997; 272:26953-8.
Schneider C, Bohnenstengel F I, Nugroho B W, Wray V, Witte L, Hung P D, Kiet L C, Proksch P. Insecticidal rocaglamide derivatives from *Aglaia spectabilis* (Meliaceae). Phytochemistry 2000; 54:731-6.
Trauth B C, Klas C, Peters A M, et al. Monoclonal antibody-mediated tumor regression by induction of apoptosis. Science. 1989; 245:301-305.
Vermes I, Haanen C, Reutelingsperger C. Flow cytometry of apoptotic cell death. J Immunol Methods. 2000; 243:167-190
Walczak H, Miller R E, Ariail K, et al. Tumoricidal activity of tumor necrosis factor-related apoptosis-inducing ligand in vivo. Nat. Med. 1999; 5:157-163.
Zhu, J Y., Lavrik, I. N., Mahlknecht, U., Giaisi, M., Proksch, P., Krammer, P H., and Li-Weber, M. The Tradition Chinese Herbal Compound Rocaglamide Preferentially Induces Apoptosis in Leukemia Cells by Modulation of MAPK Activities Int. J. Cancer, 2007; 121:1839-1846.
Zhu J Y, Giaisi M, Köhler R, Müller W W, Mühleisen A, Proksch P, Krammer P H, Li-Weber M. Rocaglamide sensitizes leukemic T cells to activation-induced cell death by differential regulation of CD95L and c-FLIP expression. Cell Death Differ. 2009; 16:1289-1299.

The invention claimed is:

1. A pharmaceutical preparation for treating death-receptor ligand resistant Hodgkin lymphoma or human T-cell leukemia virus type 1 (HTLV-1)-associated adult T-cell leukemia/lymphoma (ATL), comprising a therapeutically effective amount of:
a) at least one rocaglamide derivative of the formula (I) and/or a pharmaceutically acceptable salt thereof; and
b) TRAIL,
wherein the compound of formula (I) has the following structure:

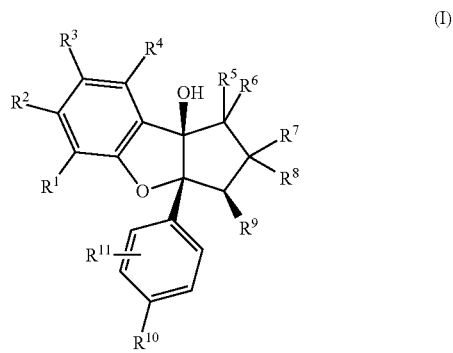

(I)

wherein:
$R^1$ is selected from hydrogen, halogen and alkyl;
$R^2$ is selected from halogen, alkyl and alkoxy;
$R^3$ is selected from hydrogen, halogen and alkyl;
$R^4$ is selected from halogen, alkyl and alkoxy;
or $R^2$ and $R^3$ together form a —OCH$_2$CH$_2$O— unit;
$R^5$ is selected from hydroxyl, acyloxy, amino, monoalkylamino, dialkylamino and —NR$^{12}$—CHR$^{13}$—COOR$^{14}$, with R$^{12}$ being selected from hydrogen and alkyl, R$^{13}$ being selected from phenyl and benzyl, which both may carry a substituent from the group hydroxyl, indolyl and imidazolylmethyl, and alkyl which may be substituted by a group selected from OH, SH, alkoxy, thioalkoxy, amino, monoalkylamino, dialkylamino, carboxy, carboxyalkyl, carboxamide and hydroxyl groups; or $R^{12}$ and $R^{13}$ together form a —$(CH_2)_3$— or —$(CH_2)_4$— group;

$R^{14}$ being selected from alkyl and benzyl; in which case $R^6$ is hydrogen, or $R^5$ and $R^6$ together form an oxo or hydroxyimino group;

$R^7$ is hydrogen;

$R^8$ is selected from hydrogen, —$COOR^{15}$ and $CONR^{16}R^{17}$, wherein $R^{15}$ and $R^{16}$ are independently selected from hydrogen and methyl, and $R^{17}$ is selected from hydrogen, methyl, 4-hydroxybutyl and 2-tetrahydrofuryl;

$R^9$ is selected from phenyl which is optionally substituted, and hetaryl which is optionally substituted;

$R^{10}$ is selected from hydrogen, halogen, alkyl and alkoxy, and $R^{11}$ is selected from hydrogen, hydroxyl, halogen, alkoxy and alkyl; or $R^{10}$ and $R^{11}$ are in ortho-position to each other and together form a —$OCH_2O$— unit;

or a pharmaceutically acceptable salt thereof.

2. The preparation according to claim 1, wherein the substituents $R^1$ to $R^{14}$ have the following meanings:

$R^1$ and $R^3$ each are hydrogen;

$R^2$ and $R^4$ each are independently selected from methoxy which is optionally substituted;

$R^5$ is selected from hydroxy, formyloxy and acetyloxy, alkylamino, and —$NR^{12}$—$CHR^{13}$—$COOR^{14}$, with (a) $R^{12}$ being selected from hydrogen and alkyl, (b) $R^{13}$ being selected from: alkyl which may be substituted by: a group selected from OH, SH, alkoxy; thioalkoxy, amino, monoalkylamino, dialkylamino, carboxy, carboxyalkyl, carboxamide and guanidino groups; and phenyl and benzyl, which both may carry a substituent from the group hydroxy, indolyl and imidazolylmethyl; and (c) $R^{14}$ being selected from alkyl and benzyl;

$R^6$ is hydrogen;

$R^7$ is hydrogen;

$R^8$ is selected from hydrogen, —$COOCH_3$ and $CON(CH_3)_2$;

$R^9$ is phenyl which is optionally substituted;

$R^{10}$ is methoxy;

$R^{11}$ is selected from hydrogen and hydroxy, or $R^{10}$ and $R^{11}$ are in ortho-position to each other and together form a —$OCH_2O$— unit.

3. A method for preparing the pharmaceutical preparation of claim 1, comprising admixing in a suitable amount the rocaglamide derivative of formula (I), TRAIL, and at least one pharmaceutically acceptable carrier.

4. A method for treatment of cancer in a patient comprising administering a preparation of claim 1 to the patient.

5. The method of claim 4, wherein the patient is a human.

6. The preparation according to claim 1, wherein the preparation comprises the rocaglamide derivative mixed with TRAIL.

7. The preparation according to claim 1 for treating TRAIL-resistant Hodgkin lymphoma or HTLV-1-associated ATL, wherein the rocaglamide derivative is selected from the group consisting of:

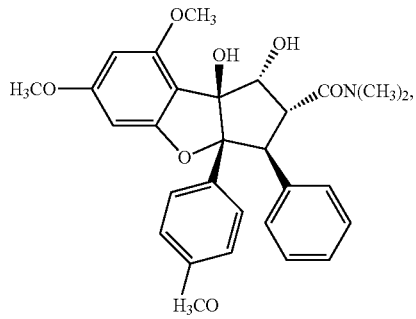

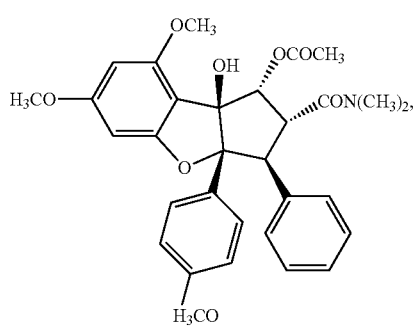

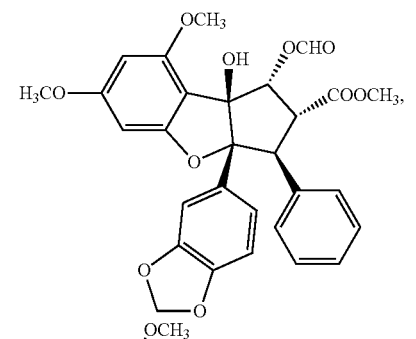

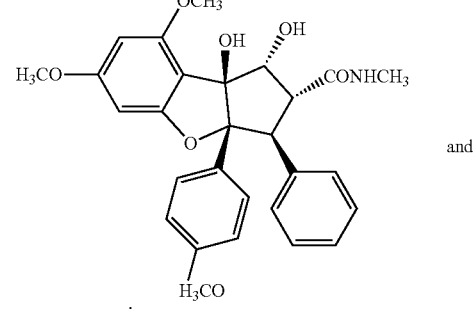

and

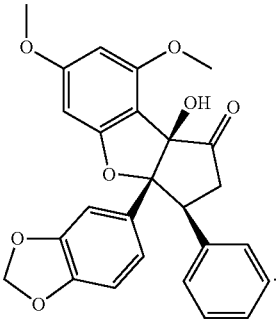

8. The preparation according to claim 1 for treating TRAIL-resistant Hodgkin lymphoma or HTLV-1-associated ATL, wherein the rocaglamide derivative is:

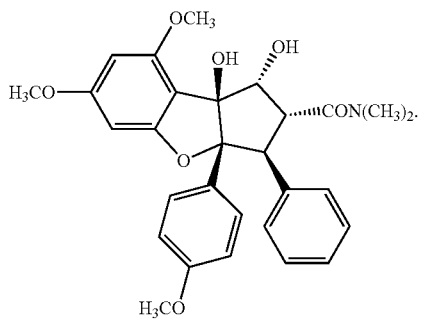

9. The preparation according to claim 1 for treating TRAIL-resistant Hodgkin lymphoma or HTLV-1-associated ATL, wherein the rocaglamide derivative is:

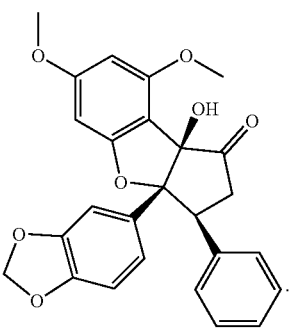 [SMILES: COc1cc(OC)c2c(c1)O[C@@]1(c3ccc4c(c3)OCO4)[C@H](c3ccccc3)CC(=O)[C@@]21O]

10. The preparation according to claim 7, wherein the preparation further comprises XIAP inhibitor.

11. The preparation according to claim 8, wherein the preparation further comprises XIAP inhibitor.

12. The preparation according to claim 9, wherein the preparation further comprises XIAP inhibitor.

* * * * *